US012685505B2

(12) United States Patent
He et al.

(10) Patent No.: US 12,685,505 B2
(45) Date of Patent: Jul. 21, 2026

(54) RADIOGRAPHIC IMAGING METHOD AND APPARATUS

(71) Applicant: SHENZHEN MINDRAY BIO-MEDICAL ELECTRONICS CO., LTD., Shenzhen (CN)

(72) Inventors: Hongqi He, Shenzhen (CN); Peng Xu, Shenzhen (CN); Shuangshuang Li, Shenzhen (CN); Jiye Zhang, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 164 days.

(21) Appl. No.: 18/597,806

(22) Filed: Mar. 6, 2024

(65) Prior Publication Data

US 2025/0148602 A1 May 8, 2025

(30) Foreign Application Priority Data

Nov. 6, 2023 (CN) .......................... 202311470358.6

(51) Int. Cl.
*G06T 7/00* (2017.01)
*A61B 6/00* (2006.01)
(Continued)

(52) U.S. Cl.
CPC ............ *G06T 7/0014* (2013.01); *A61B 6/463* (2013.01); *A61B 6/488* (2013.01); *A61B 6/54* (2013.01); *G06T 7/248* (2017.01); *G06T 7/74* (2017.01); *G06T 11/26* (2026.01); *G06T 11/60* (2013.01); *G06T 2200/24* (2013.01); *G06T 2207/10116* (2013.01); *G06T 2207/20104* (2013.01); *G06T 2207/30004* (2013.01); *G06T 2207/30196* (2013.01)

(58) Field of Classification Search
CPC .......... G06T 7/0014; G06T 7/74; G06T 7/248
See application file for complete search history.

(56) References Cited

U.S. PATENT DOCUMENTS

2015/0251019 A1* 9/2015 Rigney ................ A61N 5/1049
                                                                        600/1
2017/0273614 A1* 9/2017 Giphart ................ A61B 6/5217
(Continued)

OTHER PUBLICATIONS

Extended European Search Report dated Sep. 4, 2024, issued in related European Patent Application No. 24164751.0 (8 pages).

*Primary Examiner* — Hugh Maupin
(74) *Attorney, Agent, or Firm* — Sheppard Mullin Richter & Hampton LLP

(57) ABSTRACT

A radiographic imaging method includes: obtaining a posture image of an object under examination located at a shooting position between a radiation source and a detector; obtaining items concerning posture from an image based on the posture image, the items concerning posture including a region of interest of the object under examination, an imaging plane region of the detector and a radiation field region of the radiation source on the object under examination; obtaining range information and/or position information about the region of interest, the imaging plane region and the radiation field region based on the items concerning posture; and performing posture quality control using the range information and/or the position information.

18 Claims, 19 Drawing Sheets

(51) Int. Cl.

| | |
|---|---|
| *A61B 6/46* | (2024.01) |
| *G06T 7/246* | (2017.01) |
| *G06T 7/73* | (2017.01) |
| *G06T 11/26* | (2026.01) |
| *G06T 11/60* | (2006.01) |

(56) References Cited

U.S. PATENT DOCUMENTS

| | | | |
|---|---|---|---|
| 2019/0090955 A1* | 3/2019 | Singh | A61B 17/00 |
| 2019/0117183 A1 | 4/2019 | Lundt | |
| 2020/0029919 A1 | 1/2020 | Senegas et al. | |
| 2020/0218922 A1* | 7/2020 | Chen | A61B 6/469 |
| 2020/0268339 A1* | 8/2020 | Hao | A61B 6/544 |
| 2021/0121137 A1 | 4/2021 | Vanhooser | |
| 2021/0350532 A1* | 11/2021 | Kimmel | A61B 5/721 |
| 2021/0353244 A1* | 11/2021 | Kiely | A61N 5/1037 |
| 2024/0206973 A1* | 6/2024 | Charest | A61B 17/86 |
| 2024/0350109 A1* | 10/2024 | Sevenster | G16H 30/40 |
| 2025/0017548 A1* | 1/2025 | Shen | A61B 6/4085 |
| 2025/0302335 A1* | 10/2025 | Chaudhury | A61B 5/1113 |

* cited by examiner

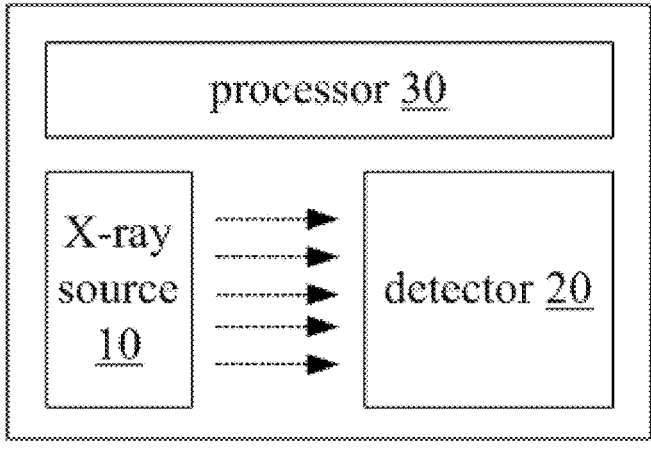
FIG. 1
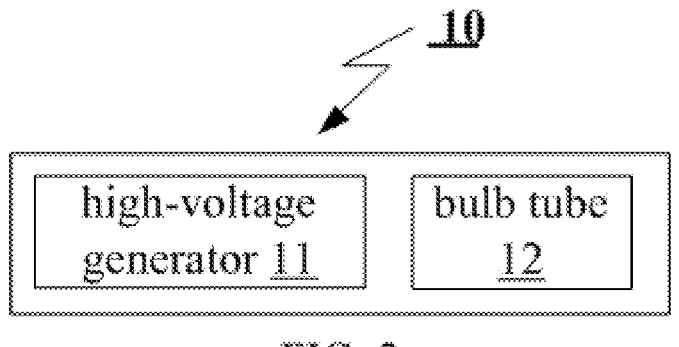
FIG. 2
FIG. 3 rays ray conversion layer    21 visible light

TFT matrix layer    22 electrical
signals

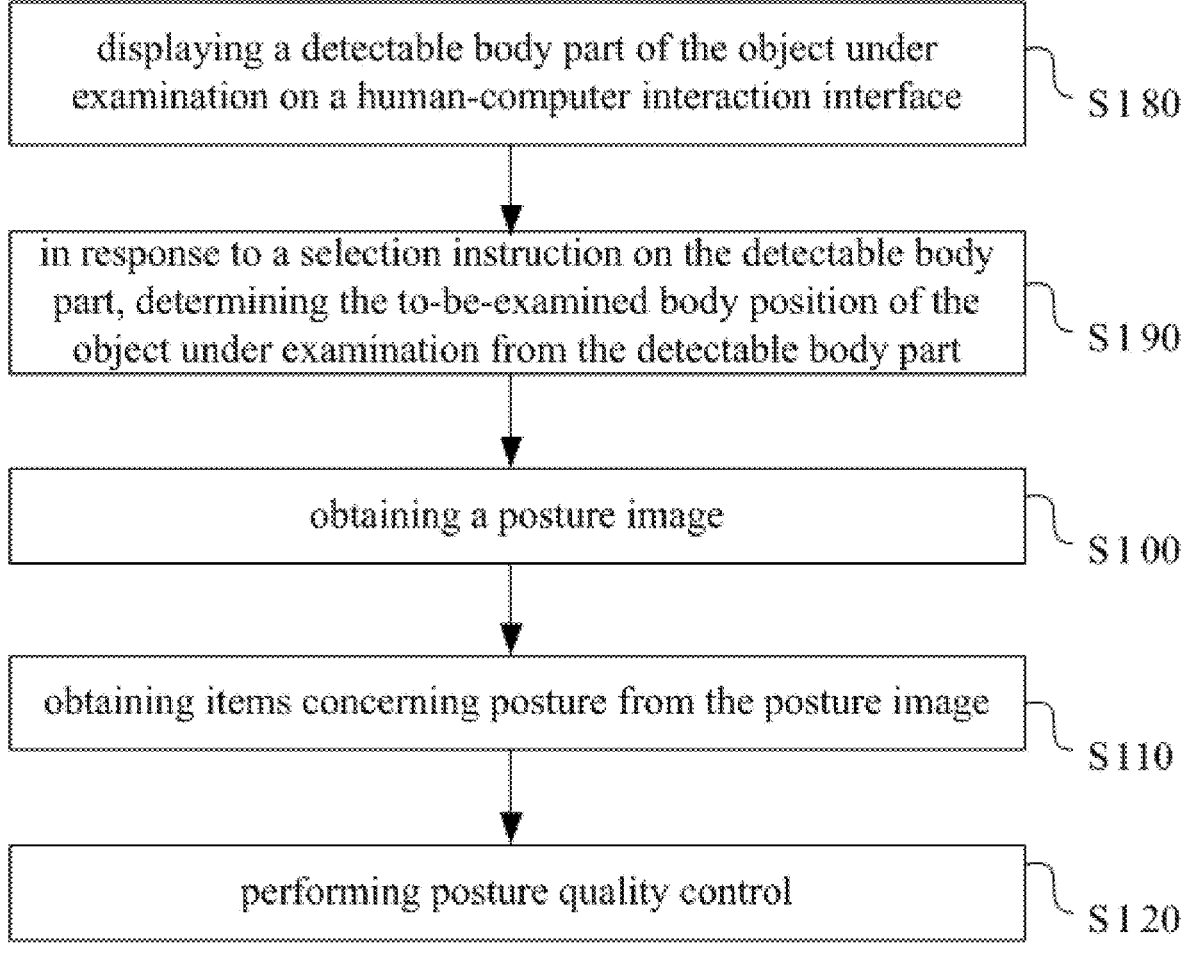

displaying a detectable body part of the object under examination on a human-computer interaction interface — S180 in response to a selection instruction on the detectable body part, determining the to-be-examined body position of the object under examination from the detectable body part — S190 obtaining a posture image — S100 obtaining items concerning posture from the posture image — S110 performing posture quality control — S120

FIG. 11 obtaining a posture image — S 100 obtaining items concerning posture from the posture image — S110 performing posture quality control — S 120 motion detecting after positioning — S 130 obtaining a posture image — S 100 obtaining items concerning posture from the posture image — S110 performing posture quality control — S 120 obtaining and outputting a prompt item — S 140 obtaining a posture image

S 100 obtaining items concerning posture from the posture image

S110 performing posture quality control

S 120 generating and outputting a guidance item

S 150

20

_100_

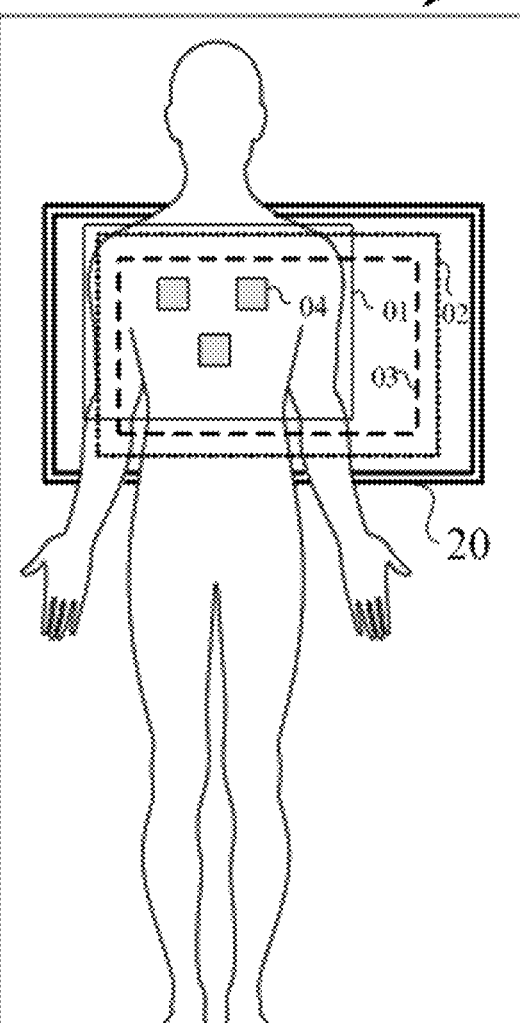

body position in image: ___PA chest___
to-be-examined body position: PA chest position matching degree (millimeter)
ROI and imaging plane region
center difference (120,30)
edge difference (54,60,184,20)

ROI and radiation field region
center difference (120,30)
edge difference (80,30,133,10)

posture requirement(s):
placing hands on hip or embracing flat
panel detector, bending elbows, forward
as much as possible, turning shoulders
inward and laying them flat current posture information:
hands placed on hip, elbows bended,
forward, shoulders turned inward and
laid flat foreign object affecting imaging:
No foreign object in ROI F I G . 1 5 ( b )

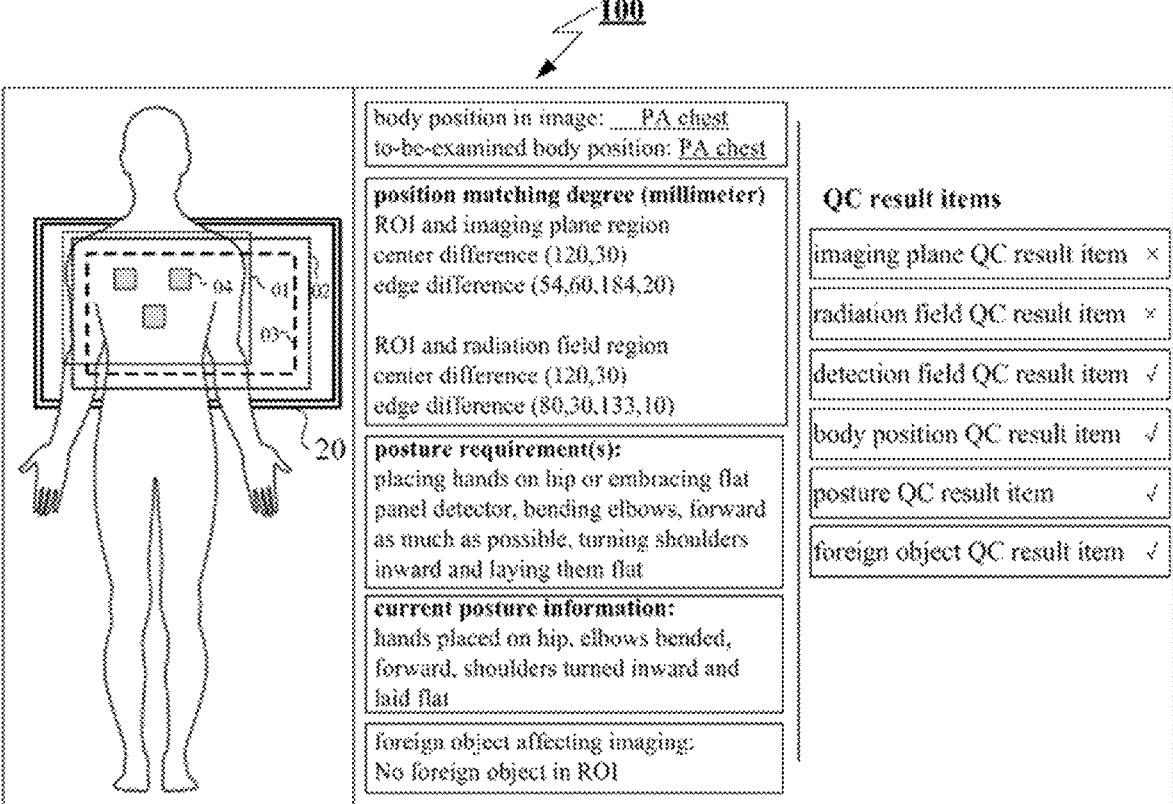
F I G . 1 5 ( e )

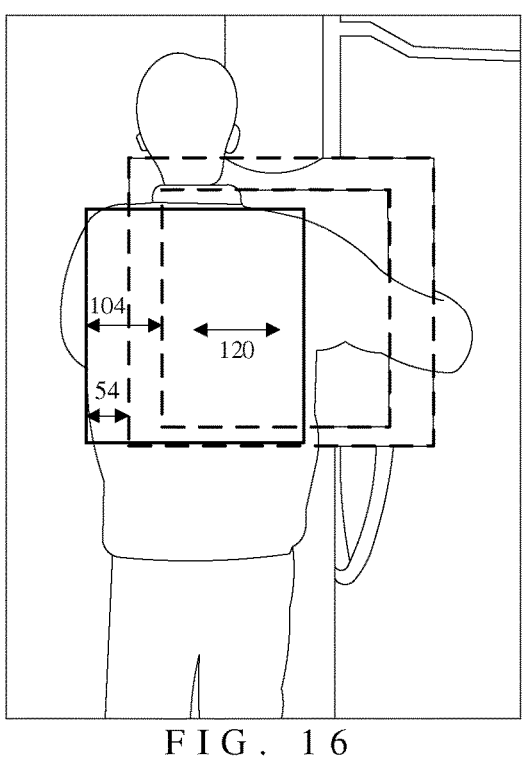

FIG. 16

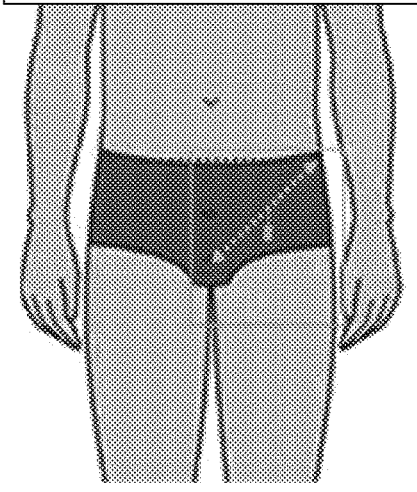

standard posture image posture requirements 2.5cm below from a perpendicular bisector of a line connecting anterior superior iliac spine and superior margin of pubic symphysis and the detector injected vertically vertical lower limbs, with slightly inward rotation of feet displaying hip joint, 1/3 of proximal femur
displaying hip joint, 1/3 of proximal femur, ipsilateral pubis, ischial bone and partial iliac bone

FIG. 17

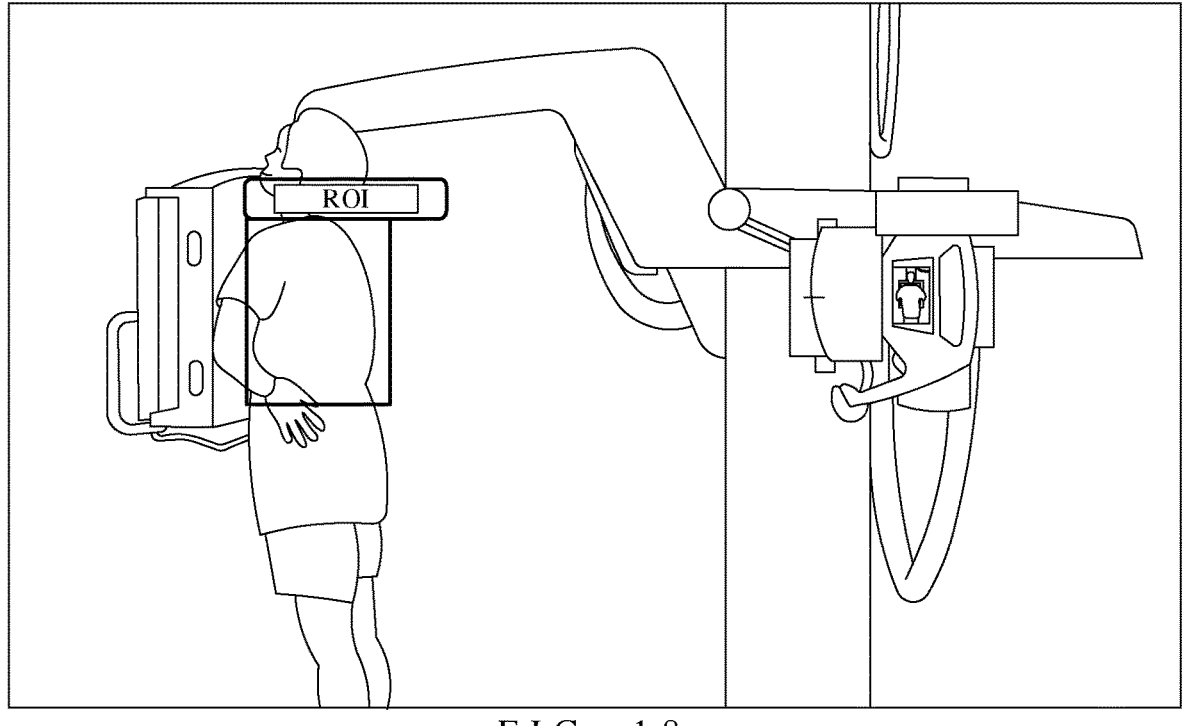
F I G .  1 8

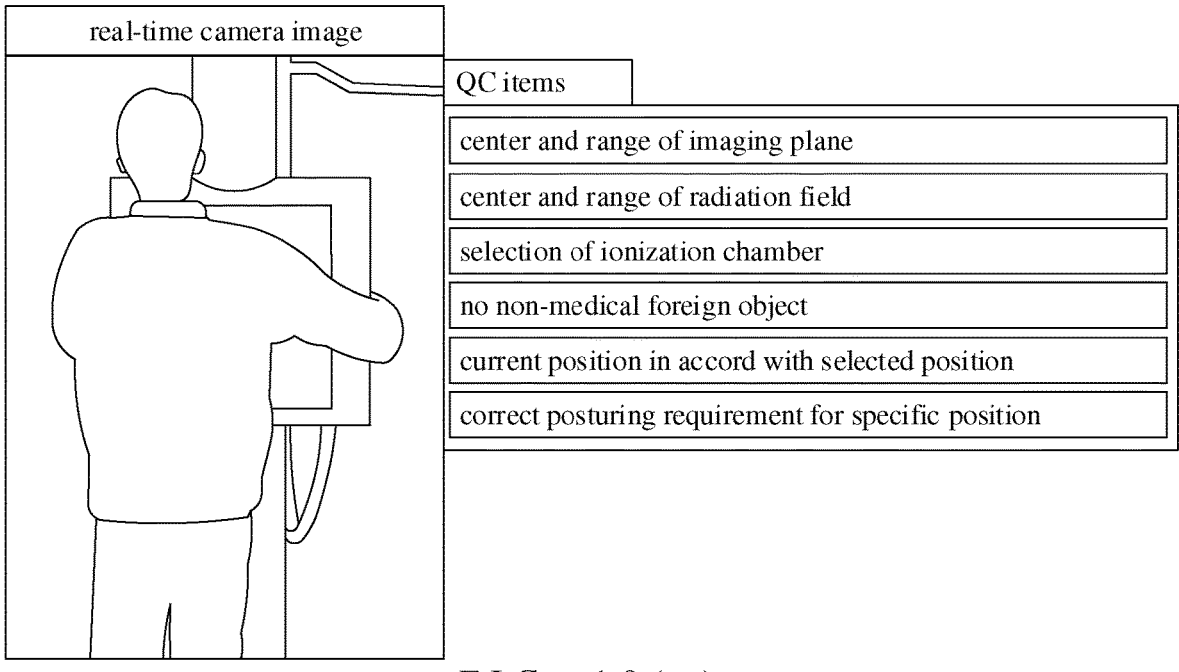
F I G .   1 9 ( a )
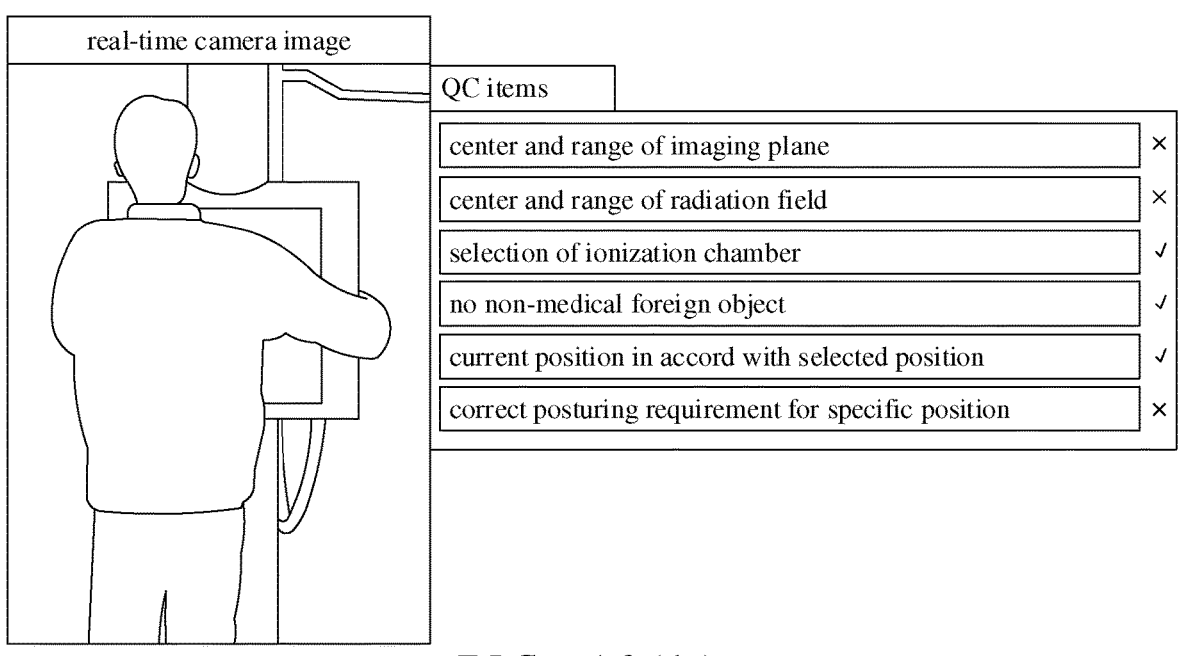
F I G .   1 9 ( b )

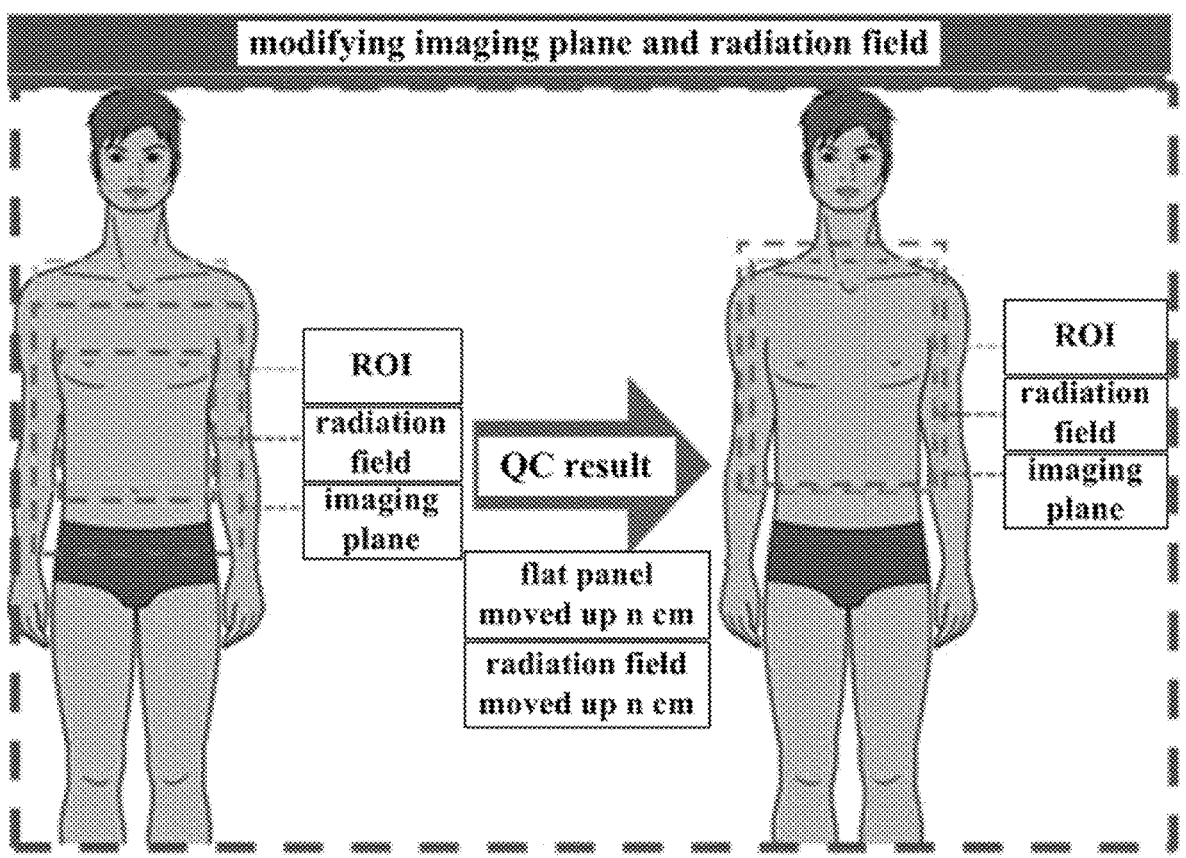
F I G .   2 0 ( a )

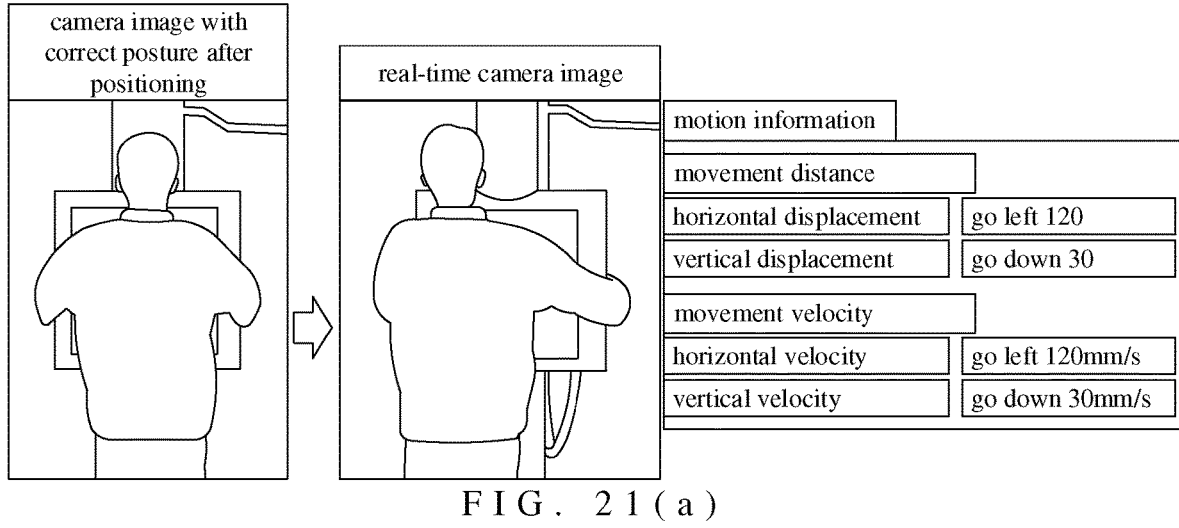
F I G .  2 1 ( a )
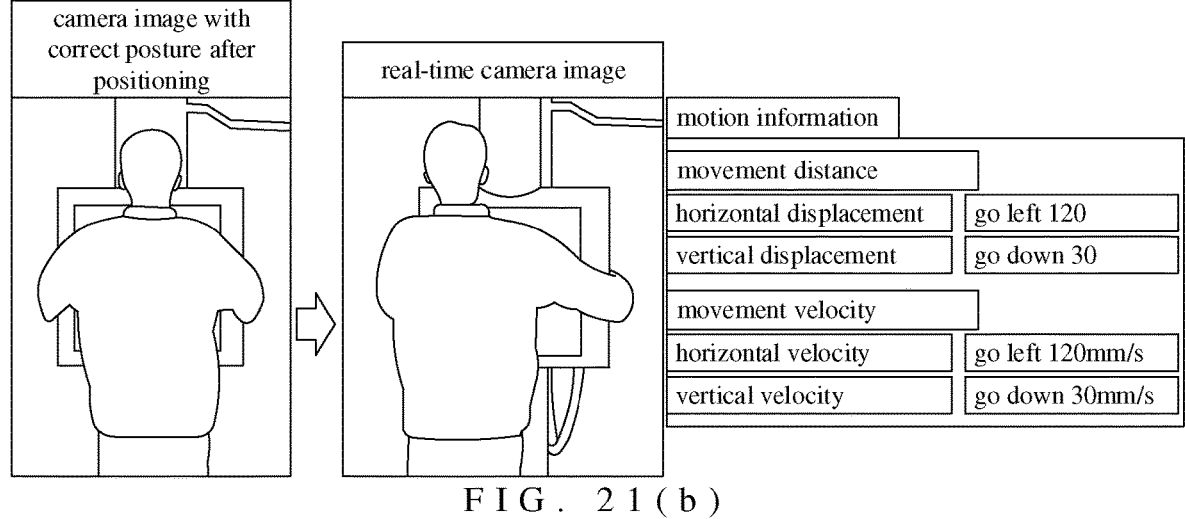
F I G .  2 1 ( b )

RADIOGRAPHIC IMAGING METHOD AND APPARATUS

CROSS-REFERENCE TO RELATED APPLICATIONS

The application is based on and claims priority to and benefits of Chinese Patent Application No. 202311470358.6, filed on Nov. 6, 2023. The entire content of the above-referenced application is incorporated herein by reference.

TECHNICAL FIELD

The present disclosure relates to radiographic imaging, in particular to radiographic imaging methods and apparatus thereof.

BACKGROUND OF THE INVENTION

As a common imaging system in medical digital imaging, a radiographic imaging apparatus is widely used in physical examination and routine medical imaging diagnosis. The radiographic imaging apparatus is a device that uses radio-active rays (such as X-rays) to penetrate an object under examination for imaging.

Taking a digital radiography (DR) equipment as an example, due to its advantages of fast imaging speed, low radiation dose, clear and delicate image, and full-body examination, it has been widely used in clinical examination and has become one primary auxiliary means for doctors to diagnose. Positioning is an important part of a process for radiographers to perform examinations. There are many requirements for positioning; for example, placing the radio-graphing area of the object under examination within an imaging plane and a radiation field and meeting require-ments to prevent incomplete coverage of a diagnosis area or excessive radiation hazards; for another example, adjusting the overall or partial posture of the object under examination to meet radiographing requirements.

In practice, radiographers rely mainly on their own sub-jective experience for the pre-exposure operation process, lacking lack of objective evaluation and measurement tools. In addition, there are a large number of body positions, making it difficult for radiographers to ensure that all aspects of the positioning of the object under examination meet the positioning standards.

SUMMARY OF THE INVENTION

Considering the above problem, radiographic imaging methods and apparatus are provided by the present disclo-sure, as detailed below.

According to a first aspect, a radiographic imaging method provided in some embodiments may include:

obtaining a posture image, the posture image being an image of an object under examination located at a shooting position between a radiation source and a detector;

obtaining items concerning posture from an image based on the posture image, the items concerning posture including a region of interest of the object under examination, an imaging plane region of the detector and a radiation field region of the radiation source on the object under examination; and obtaining range information and/or position information about the region of interest, the imaging plane region and the radiation field region based on the items concerning posture, the range information and/or the position information being used for performing posture quality control.

In some embodiments, performing posture quality control using the range information and/or the position information may comprise: calculating a position matching degree based on the range information and/or the position information, said position matching degree including: a position match-ing degree between the region of interest and the imaging plane region, and a position matching degree between the region of interest and the radiation field region; and per-forming posture quality control by displaying said position matching degree.

In some embodiments, the items concerning posture may further include one or more of: a detection field region of a dose estimation unit, a body position of the object under examination presented in the posture image, posture require-ment(s), a current posture information about the object under examination associated with the posture requirement (s), and a foreign object affecting imaging.

In some embodiments, the method may further include: performing posture quality control by displaying one or more of the items concerning posture.

In some embodiments, displaying one or more of the items concerning posture may comprise: generating and displaying a posture quality control image comprising an auxiliary image, the posture quality control image further comprising one or more of the items concerning posture, and the auxiliary image being the posture image or a schematic image obtained based on the posture image.

In some embodiments, the region of interest, the imaging plane region and the radiation field region may be displayed by superimposing a schematic graph onto the auxiliary image contained in the posture quality control image, pref-erably, the schematic graph including a region defined by lines;

and/or, the region of interest, the imaging plane region and the radiation field region may be displayed in a form of text and coordinate on the posture quality control image;

and/or, the position matching degree may be displayed in a form of text and coordinate on the posture quality control image.

In some embodiments, the position matching degree may be displayed by labelling a deviation size on a region defined by lines on the posture quality control image, wherein the deviation size may include one or more of: a boundary deviation size, a corner deviation size and a center deviation size.

In some embodiments, obtaining items concerning pos-ture from an image based on the posture image may com-prise: displaying the posture image, receiving a region selecting instruction from a user on the posture image to determine the region of interest; or, identifying an anatomi-cal structure associated with a to-be-examined position of the object under examination from the posture image, and generating the region of interest based on the anatomical structure.

In some embodiments, obtaining items concerning pos-ture from an image based on the posture image may com-prise:

obtaining a posture requirement(s) associated with the to-be-examined position of the object under examina-tion;

identifying an anatomical structure associated with a to-be-examined position of the object under examina-tion from the posture image; and determining the current posture information about the object under examination associated with the posture requirement(s) based on the posture requirement(s) and the identified anatomical structure.

In some embodiments, the method may further include: obtaining the posture image after positioning, determining whether the object under examination is moving based on the posture image after positioning and a subsequent obtained posture image, and, when determining that the object under examination is moving, generating prompt information for indicating a motion state.

In some embodiments, displaying the items concerning posture may comprise: displaying by projection, wherein:

the region of interest is displayed by projecting it onto the object under examination, a position of the projected and displayed region of interest being coincided with a position of an actual region of interest of the object under examination;

and/or, the imaging plane region is displayed by projecting it onto the object under examination, a position of the displayed imaging plane region projected being coincided with a position of an actual imaging plane region of the detector;

and/or, the radiation field region is displayed by projecting it onto the object under examination, a position of the displayed radiation field region projected being coincided with a position of an actual radiation field of the radiation source;

and/or, the detection field region is displayed by projecting it onto the object under examination, a position of the projected and displayed detection field region being coincided with a position of an actual detection field region of the dose estimation unit;

and/or, the position matching degree is displayed by projecting it onto the object under examination.

In some embodiments, the posture image is acquired in real time, and when the posture image changes, the items concerning posture are updated in real time.

In some embodiments, performing posture quality control using the range information and/or the position information may comprise: performing quality control based on the range information and/or the position information to obtain quality control (QC for short) result items including an imaging plane QC result item and a radiation field QC result item, the imaging plane QC result item being a QC result indicating whether a range and/or a position of the region of interest and that of the imaging plane region meet requirements, and the radiation field QC result item being a QC result indicating whether a range and/or a position of the region of interest and that of the radiation field region meet requirements; and performing posture quality control by displaying the imaging plane QC result item and the radiation field QC result item.

In some embodiments, the method may further include: obtaining QC result items based on the items concerning posture, the QC result items further comprising one or more of: a detection field QC result item, a body position QC result item, a posture QC result item and a foreign object QC result item; the body position QC result item being a QC result indicating whether the body position of the object under examination presented in the posture image meet requirements, the posture QC result item being a QC result indicating whether the current posture information about the object under examination associated with the posture requirement(s) meet requirements, the detection field QC result item being a QC result indicating whether the detection field region is within the region of interest and/or whether the detection field region should be selected to be opened, and the foreign object QC result item being a QC result indicating whether there is a foreign object and/or whether there is a foreign object in the region of interest; and displaying one or more of the detection field QC result items, the body position QC result item, the posture QC result item and the foreign object QC result item.

In some embodiments, the imaging plane QC result item is used for indicating: whether respective centers of the region of interest and the imaging plane region are within a preset deviation, and/or whether respective boundaries of the region of interest and the imaging plane region are within a preset deviation;

and/or, the radiation field QC result item is used for indicating: whether respective centers of the region of interest and the radiation field region are within a preset deviation, and/or whether respective boundaries of the region of interest and the radiation field region are within a preset deviation;

and/or, the body position QC result item is used for indicating whether the body position of the object under examination presented in the posture image is the to-be-examined position of the object under examination;

and/or, the posture QC result item is used for indicating whether, in the current posture information about the object under examination associated with the posture requirement(s), posture information about the anatomical structure associated with a to-be-examined position of the object under examination is conformed to a posture required by the posture requirement(s) associated with the to-be-examined position of the object under examination.

In some embodiments, the method may further include: obtaining a prompt item based on the QC result items, the prompt item being used for indicating a result caused due to the QC result items failing to meet requirements; and outputting the prompt item.

In some embodiments, the method may further include: obtaining a guidance item based on the QC result items, the guidance item being used for indicating an execution action to be guided due to the QC result items failing to meet requirements; and outputting the guidance item; and/or controlling a device to carry out the execution action based on the guidance item.

In some embodiments, the guidance item may comprise at least one of:

a guidance prompt for a position and/or an angle of the detector;

a guidance prompt for a position and/or an angle of the radiation source;

a guidance prompt for a size of the radiation field region;

a guidance prompt for selecting the detection field region;

a prompt for guiding movement of the object under examination so that the imaging plane QC result item and/or the radiation field QC result item meet requirements; and a prompt for guiding a posture of the object under examination so that the body position QC result item and/or the posture QC result item meet requirements.

In some embodiments, the method may further include: displaying a detectable body part of the object under examination on a human-computer interaction interface; and in response to a selection instruction on the detectable body part, determining the to-be-examined position of the object under examination from the detectable body part.

According to a second aspect, a radiographic imaging apparatus provided in some embodiments may include:

a radiation source configured to emit radioactive rays to an object under examination;

a detector configured to receive the radioactive rays penetrating the object under examination; and a processor configured to execute the method according to any one of the embodiments mentioned herein.

With the radiographic imaging methods and apparatus mentioned in aforesaid embodiments, a quantitative or qualitative scheme can be proposed to assist users in posture quality control by obtaining a posture image and obtaining items concerning posture based on the posture image to further obtain range information and/or position information about the region of interest, the imaging plane region and the radiation field region, and performing posture quality control based on the range information and/or the position information.

With the radiographic imaging methods and apparatus mentioned in aforesaid embodiments, a posture image may be obtained so as to obtain items concerning posture based thereupon, a position matching degree may also be calculated, and relevant information may be displayed for user viewing, accordingly, users can determine whether to readjust the positioning and how to adjust the positioning based on the identified items concerning posture, which is very convenient.

With the radiographic imaging methods and apparatus mentioned in aforesaid embodiments, a posture image may be obtained so as to obtain items concerning posture based thereupon, then quality control may be performed automatically based on the items concerning posture to obtain QC result items which can be displayed on a display component for radiographers to view.

BRIEF DESCRIPTION OF THE DRAWINGS

FIG. 1 is a schematically structural diagram of a radiographic imaging apparatus in some embodiments;

FIG. 2 is a schematically structural diagram of a radiation source in some embodiments;

FIG. 3 is a schematically structural diagram of a radiation source in some embodiments;

FIG. 11 is a schematic flowchart of a radiographic imaging method in some embodiments;

FIG. 15(b) is an example diagram of a posture quality control image in some embodiment, FIG. 15(e) is an example diagram of a posture quality control image in some embodiment;

FIG. 16 is an example diagram of displaying items concerning posture in some embodiment;

FIG. 17 is an example diagram of displaying posture requirement(s) in some embodiment;

FIG. 18 is an example diagram of displaying items concerning posture by projection in some embodiment;

FIG. 19(a) is an example diagram of displaying QC result items in some embodiment, and FIG. 19(b) is an example diagram of displaying QC result items in some other embodiment;

FIG. 20(a) is an example diagram of displaying a guidance item in some embodiment, FIG. 21(a) is an example diagram of motion detection and display after positioning in some embodiment, and FIG. 21(b) is an example diagram of motion detection and display after positioning in some embodiment.

DETAILED DESCRIPTION

Figure 4:
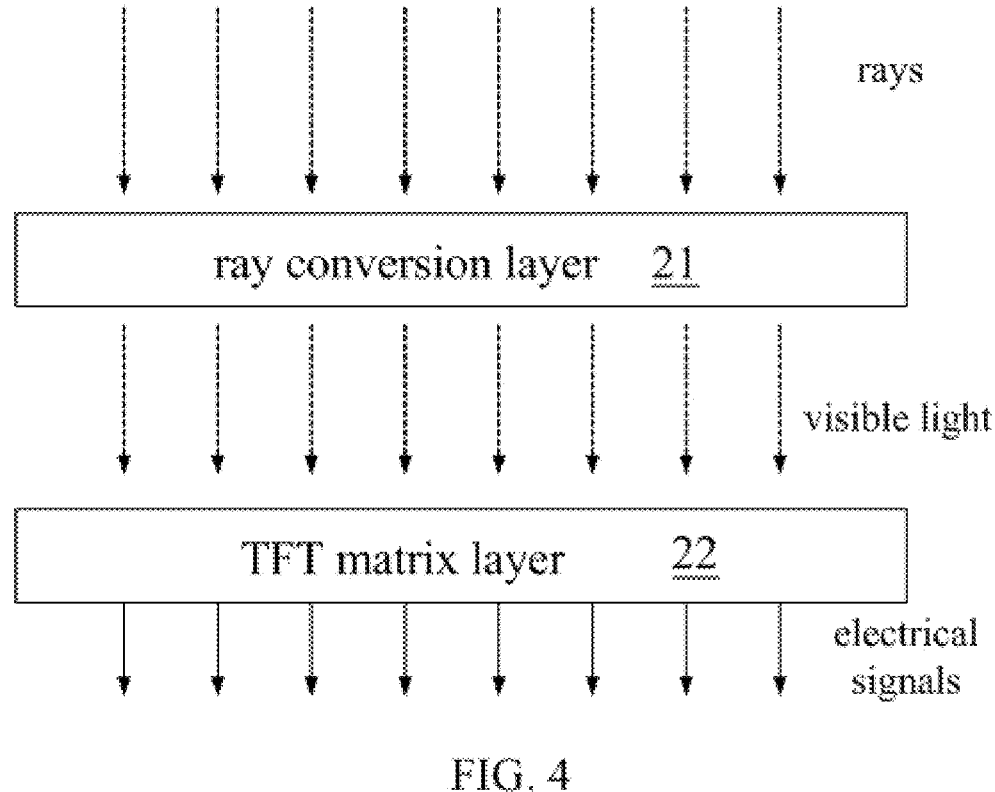
FIG. 4 is a schematically structural diagram of a detector in some embodiments.

The present disclosure is further described in detail below through specific embodiments in combination with the drawings, wherein, similar elements in different embodiments adopt associated similar element labels. In the following embodiments, many details are described in order to make the application be better understood. However, those skilled in the art can easily realize that some features can be omitted in different cases or can be replaced by other elements, materials and methods. In some cases, some operations related to the present disclosure are not shown or described in the specification in order to avoid the core part of the present disclosure being overwhelmed by excessive descriptions, and for those skilled in the art, it is not necessary to describe these relevant operations in detail, they can completely understand the relevant operations according to the description in the specification and the general technical knowledge of the field.

In addition, the features, operations or characteristics described in the specification may be combined in any appropriate manner to form various embodiments. At the same time, the steps or actions described in the method may be sequenced or adjusted in a manner apparent to those skilled in the art. Therefore, the sequences in the specification and the drawings are intended to clearly describe an embodiment and are not meant to be a required sequence unless it is indicated otherwise that a sequence must be followed.

The serial numbers assigned to the parts in the present disclosure, such as "first", "second", etc., are only used to distinguish the described objects, and do not have any sequential or technical meaning. The terms "connect" and "couple" as mentioned in the present disclosure, unless otherwise specified, include direct and indirect connection (coupling).

Referring to FIG. 1, a radiographic imaging apparatus provided in some embodiments may include a radiation source 10, a detector 20 and a processor 30. The radiation source 10 may be configured to emit radioactive rays, such as X-ray, to an object under examination; and the detector 20 may be configured to receive the radioactive rays penetrating the object under examination for imaging. This will be illustrated in detailed below.

In some embodiments, referring to FIG. 2, the radiation source 10 may include a high-voltage generator 11 and a ray emitter 12 which are electrically connected. The high-voltage generator 11 may be configured to provide high-voltage signals, such as hundred-volt or kilovolt high-voltage signals, to the ray emitter 12. The ray emitter 12 may be configured to bombard electrons onto a target surface under the high-voltage signals to generate radioactive rays, such as X-rays. The ray emitter 12 may be, for example, a bulb tube. The detector 20 may be configured to receive radioactive rays for imaging.

In some embodiments, referring to FIG. 3, the radiation source 10 may also include a beam limiter 13. In some embodiments, the beam limiter 13 may be configured to determine or simulate the radiation source 10 or the radiating area of the ray emitter 12. The area irradiated by the beam limiter 13 may be referred to as a radiation field or a radiation field region. Furthermore, the radiation source 10 may be configured to emit radioactive rays, and the detector 20 may be configured to receive the radioactive rays. In this process, the beam limiter 13 may also be configured to limit the radiation field of the radioactive rays emitted by the ray emitter 12. Therefore, in some examples, the beam limiter 13 may be able to constrain the radioactive rays and shield scattered radioactive rays.

The detector 20 is a crucial component of the radiographic imaging apparatus and plays a decisive role in ensuring high-quality imaging. In some embodiments, the detector 20 may be configured to receive radioactive rays (such as X-rays) and convert them into electrical signals, thereby completing the acquisition of image information. Referring to FIG. 4, the detector 20 may include a ray conversion layer 21 and a TFT matrix layer 22 in some embodiments. The ray conversion layer 21 may be configured to convert the radioactive rays (such as X-rays) into visible light. The ray conversion layer 21 may typically include a scintillation layer or a fluorescent layer for converting the rays into visible light. Taking the scintillation layer as an example, it may generally be made of scintillation materials, such as cesium iodide (CsI) or gadolinium oxysulfide (GOS). The TFT matrix layer 22 may be configured to sense the visible light converted by the ray conversion layer 21 and convert the visible light into electrical signals for acquiring image information. The detector 20 may be a flat panel detector in some embodiments.

Figure 5:
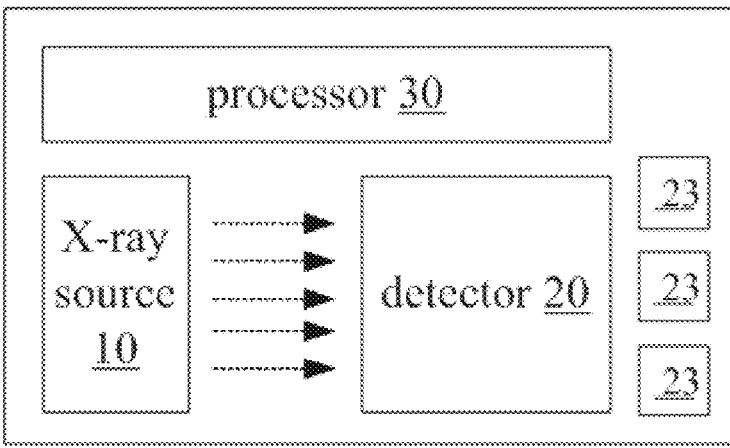
FIG. 5 is a schematically structural diagram of a radiographic imaging apparatus in some embodiments.

In some embodiments, referring to FIG. 5, the radiographic imaging apparatus may further include one or more dose estimation units configured to estimate the dose of radiation during radiographic imaging, so as to allow the processor 30 or radiation source 10 to determine the timing of receiving and emitting radioactive rays, that is, to control the exposure cut-off.

Figure 6:
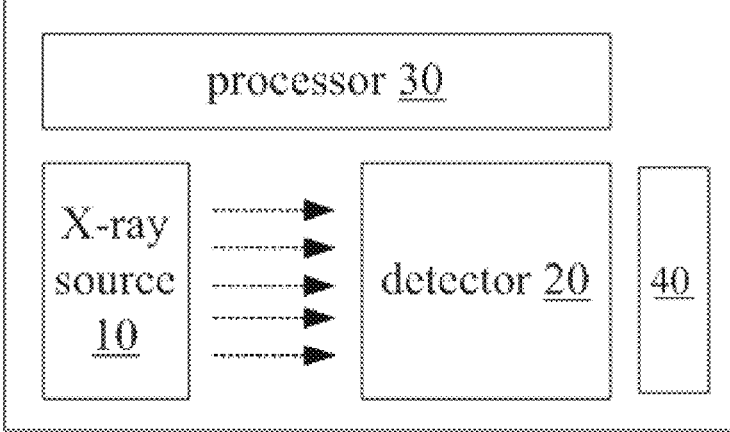
FIG. 6 is a schematically structural diagram of a radiographic imaging apparatus in some embodiments.

In some embodiments, referring to FIG. 6, the radiographic imaging apparatus may also include a camera 40; alternatively, the radiographic imaging apparatus may also be connected to a camera 40. The camera 40 may be configured to perform image acquisition, such as real-time image acquisition. In some examples, when the object under examination is located at a shooting position between the radiation source 10 and the detector 20, the camera 40 can acquire images to obtain image of the object under examination located at the shooting position between the radiation source and the detector.

Figure 7:
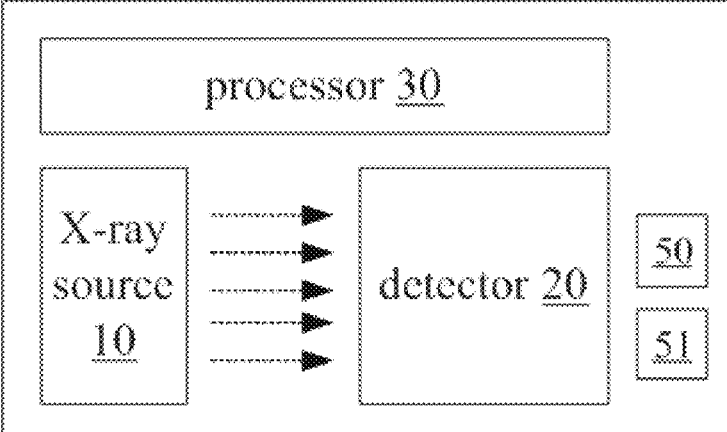
FIG. 7 is a schematically structural diagram of a radiographic imaging apparatus in some embodiments.

In some embodiments, referring to FIG. 7, the radiographic imaging apparatus may further include an output element, such as a display screen 50 or a voice playback component 51. In some embodiments, the display screen 50 may be integrated with a voice playback function. In some embodiments, the radiographic imaging apparatus may include a support structure for supporting the radiation source 10 and/or the detector 20, and the display screen 50 and/or the voice playback component 51 may be arranged on the support structure.

Figure 8:
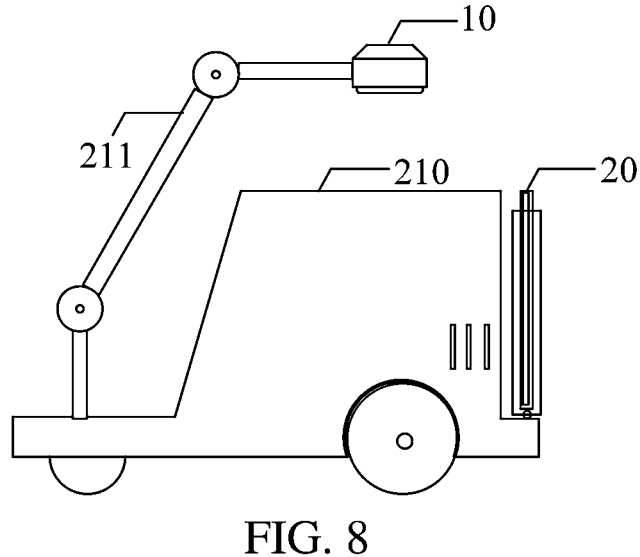
FIG. 8 is a schematically structural diagram of a radiographic imaging apparatus in some embodiments.

FIG. 8 is an example of a mobile radiographic imaging apparatus. In the figure, the support structure may include a movable body 210, a robotic arm 211 arranged on the body 210, and a radiation source 10. The robotic arm 211 may be equipped with the radiation source 10. In some embodiments, the radiation source 10 may have a housing structure for support and storage. In some embodiments, the radiation source 10 may be configured to support the ray emitter 12; for example, the ray emitter 12 may be arranged within the radiation source 10. In some embodiments, the radiation source 10 may be configured to support the high-voltage generator 11; for example, the high-voltage generator 11 may be arranged within the radiation source 10. In some embodiments, the beam limiter 13 may be arranged at the radiation source 10. The detector 20 may be a flat panel detector, which can be conveniently stored inside the body 210 when not in use. Since the body 210 of the apparatus is movable, it can be moved to a desired location for use, such as being moved to an operating room, emergency room, ICU ward, neonatal department, and critical patient isolation area. The movable body 210 may be typically equipped with a motion mechanism that can be manually actuated or electrically driven to enable movement of the apparatus. The radiation source 10 may be suspended and movably disposed on the body 210, and may be moved in two or three dimensions through the use of the robotic arm 211. The detector 20 configured for the apparatus may be wired or wireless. A wired flat panel detector 20 may be typically connected to the body 210 through cables to complete charging and data transmission functions; while a wireless flat panel detector 20 may be used by physically disconnecting from the body 210, such as when a radiographer removes the wireless flat panel detector 20 from the body 210 for use. Mobile radiographic imaging apparatus may typically equipped with wireless flat panel detectors. After receiving an exposure request, the processor 30 may control the radiation source 10 to expose, i.e., emitting radioactive rays (such as X-rays) to the object under examination, and control the wireless flat panel detector 20 to work in coordination with the radiation source 10 to receive the radioactive rays (such as X-rays) penetrated the object under examination for imaging. The imaged data may subsequently be further transmitted to the processor 30 for image processing and subsequent control for display.

Figure 9:
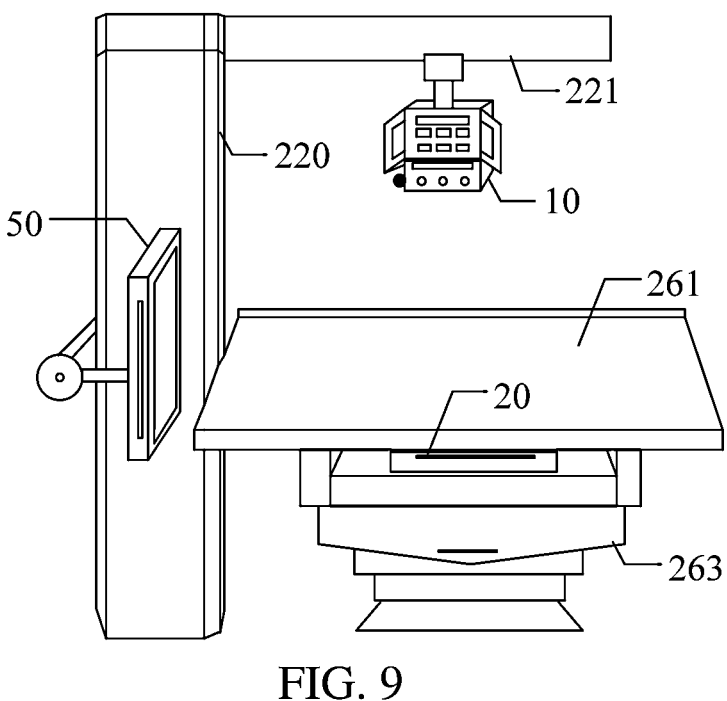
FIG. 9 is a schematically structural diagram of a radiographic imaging apparatus in some embodiments.

FIG. 9 shows an example of a fixed radiographic imaging apparatus. In the figure, the support structure may include a post 220, a slide 221 arranged on the post 220, and the radiation source 10 arranged on the slide 221. The radiation source 10 may be moved in two or three dimensions via the slide 221. In some embodiments, the radiation source 10 may have a housing structure for support and storage. In some embodiments, the radiation source 10 may be configured to support the ray emitter 12, such as placing the ray emitter 12 inside the radiation source 10. In some embodiments, the beam limiter 13 may be arranged on the radiation source 10. The apparatus may further include a bed plate 261 and a bed support structure 263 for supporting the bed plate

261. The bed plate 261 may be configured to support the object under examination, such as for the object under examination to lie down. It should be noted that the fixed radiographic imaging apparatus may be equipped with a vertically-mounted detector 20 and a horizontally-mounted detector 20, both of which may be wired. It should also be noted that the fixed radiographic imaging apparatus may be equipped with only one vertically-mounted detector 20 or one horizontally-mounted detector 20, or both detectors 20 may be equipped. In other fixed radiographic imaging apparatus, a wireless detector 20 may also be equipped, such as a fixed X-ray imaging device equipped with a wireless flat panel detector 20, or both a wireless flat panel detector 20 and a wired flat panel detector 20 may be equipped. Regardless of whether it is a wired detector 20 or a wireless detector 20, it is used to receive X-rays for imaging.

In some embodiments, the radiographic imaging apparatus may be located in a shielded room, and be operated via a computer (including a host and a display) outside the shielded room by a radiographer.

Therefore, the display component herein may be either the display screen 50 or the display included in the computer.

In some embodiments, the radiographic imaging apparatus may be a digital radiography (DR) device.

The above is some descriptions of the radiographic imaging apparatus.

In some embodiments, the processor 30 can execute the radiographic imaging method or one or more steps thereof disclosed herein.

Figure 10:
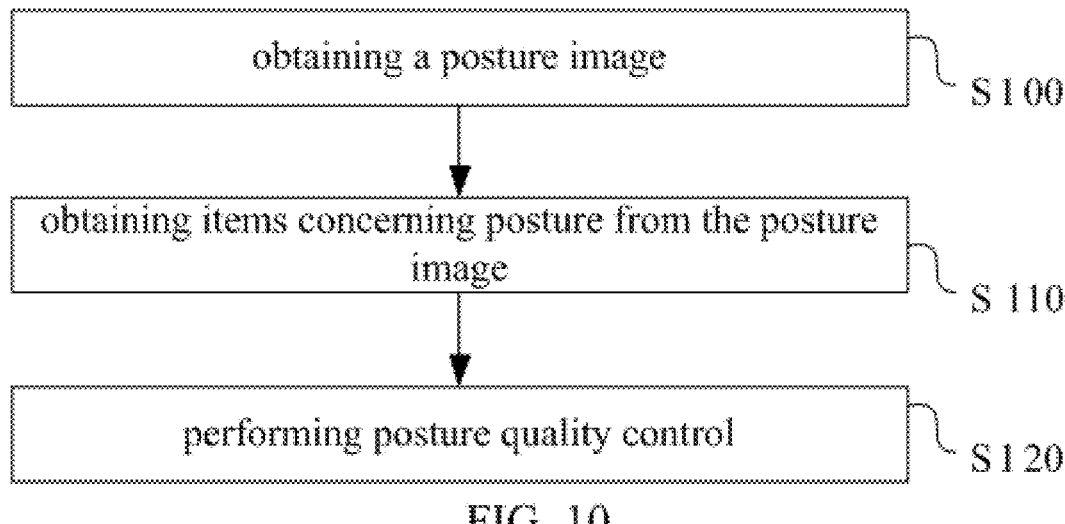
FIG. 10 is a schematic flowchart of a radiographic imaging method in some embodiments.

Referring to FIG. 10, the radiographic imaging method may include the following steps:

Step 100: obtaining a posture image, the posture image being an image of an object under examination located at a shooting position between a radiation source and a detector.

For example, the camera 40 may be used to acquire images, such as single-frame or multi-frame images, so as to obtain the posture image.

Step 110: obtaining items concerning posture from an image based on the posture image.

The inventor conducted research on positioning-related matters in clinical practice, and proposed items concerning posture which are used to assist radiographers in positioning the object under examination.

In some embodiments, the items concerning posture may include one or more of: a region of interest (ROI) of the object under examination, an imaging plane region of the detector 20, a radiation field region of the radiation source 10 irradiated on the object under examination, a detection field region of the dose estimation unit 23, a body position of the object under examination presented in the posture image, posture requirement(s), current posture information about the object under examination associated with the posture requirement(s), and a foreign object affecting imaging.

The following describes each of the items concerning posture.

The ROI of the object under examination may refer to a region of the object under examination that needs to be included in an image obtained based on radiography, that is, a region of the object under examination that needs to be diagnosed. The radiographic image of this region may be viewed by doctors for diagnosis. Generally, the ROI of the object under examination is associated with the to-be-examined position of the object under examination.

In some embodiments, in step 110, the posture image may be displayed, and the ROI may be determined by receiving a region selecting instruction onto the posture image by a user (e.g., a radiographer). For example, the posture image is displayed on the display component, then the region selecting instruction is inputted onto the posture image by the radiographer (e.g., by performing a box selecting operation on the posture image using a mouse or other tools) to specify the ROI.

In some embodiments, in step 110, an anatomical structure associated with the to-be-examined position of the object under examination may be identified from the posture image, and the region of interest may be generated based on the anatomical structure. An identification algorithm adopted in step 110 may be based on machine learning and other methods.

Taking the to-be-examined position being a posterior anterior chest (PA chest) as an example, the anatomical structure associated with the to-be-examined position may include a sixth thoracic vertebrum (T-6), apex pulmonis, posterior costophrenic angle, and bilateral skeletal thorax and soft tissue. Such anatomical structure may be identified from the posture image; and accordingly, the ROI may be generated, with T-6 as the center thereof and apex pulmonis, posterior costophrenic angle, and bilateral skeletal thorax and soft tissue as the range thereof.

Taking the to-be-examined position being anteroposterior position of shoulder joint as an example, the anatomical structure associated with the to-be-examined position may include coracoid, proximal humerus, clavicle and scapula. Such anatomical structure may be identified from the posture image; and accordingly, the ROI may be generated, with 2.5 cm below the coracoid as the center thereof and the proximal humerus, the outer ⅔ of the clavicle and the upper part of the scapula as the range thereof.

The imaging plane region of the detector 20 may refer to a region of the detector 20 where radiation can be received and sensed.

In some embodiments, in step 110, the posture image may be displayed, and the imaging plane region of the detector 20 may be determined by receiving a region selecting instruction onto the posture image by a user (e.g., a radiographer). For example, the posture image is displayed on the display component, then the region selecting instruction is inputted onto the posture image by the radiographer (e.g., by performing a box selecting operation on the posture image using a mouse or other tools) to specify the imaging plane region of the detector 20.

In some embodiments, in step 110, the detector 20 may be identified from the posture image, and the imaging plane region of the detector 20 may be generated based on the identified detector 20. Since the posture image may be an image of the object under examination located at a shooting position between the radiation source 10 and the detector 20, the posture image may also contain an image of the detector 20, and accordingly, the detector 20 may be identified from the image. For example, the detector 20 may be located by four corners of the detector 20 determined based on the identified detector 20, and the imaging plane region of the detector 20 may be generated. Identifying the detector 20 from the posture image may be based on machine learning and other methods.

In some embodiments, in step 110, the spatial position of the actual imaging plane region of the detector 20 may also be acquired based on a locatable sensor (that is, the position of the actual imaging plane region of the detector 20 in the world coordinate system), and then the position information about the imaging plane region of the detector 20 in the posture image may be obtained based on a positional transformation relationship between the posture image and the world coordinate system.

The radiation field region irradiated by the radiation source 10 onto the object under examination (hereinafter referred to as the radiation field region of the radiation source 10) may refer to the location and/or range irradiated by the rays emitted by the radiation source 10. Before taking a radiographic image, the radiation source 10 or the radiating area of the ray emitter 12 may be simulated by a radiographer using the beam limiter 13 which may irradiate a cone-shaped beam of light onto the object under examination.

In some embodiments, in step 110, the posture image may be displayed, and the radiation field region of the radiation source 10 irradiated onto the object under examination may be determined by receiving a region selecting instruction onto the posture image by a user (e.g., a radiographer). For example, the posture image is displayed on the display component, then the region selecting instruction is inputted onto the posture image by the radiographer (e.g., by performing a box selecting operation on the posture image using a mouse or other tools) to specify the radiation field region of the radiation source 10.

Since the beam limiter 13 will irradiate a cone-shaped beam of light on the body of the object under examination to simulate the radiation field region of the radiation source 10, the radiation field region of the radiation source 10 may be identified from the posture image based on an image generated by irradiating the cone-shaped beam of light onto the object under examination in step 110.

In some embodiments, in step 110, the spatial position of the actual radiation field region of the radiation source 10 may also be acquired based on a locatable sensor (that is, the position of the actual radiation field region of the radiation source 10 in the world coordinate system), and then the position information about the radiation field region of the radiation source 10 in the posture image may be obtained based on a positional transformation relationship between the posture image and the world coordinate system.

The detection field region of the dose estimation unit 23 may refer to a region of the dose estimation unit 23 where radiation can be received and sensed. In some embodiments, the dose estimation unit 23 may be turned on or off. After the dose estimation unit 23 is turned on, the detection field region of the dose estimation unit 23 may also be turned on or be effective.

In some embodiments, in step 110, the posture image may be displayed, and the detection field region of the dose estimation unit 23 may be determined by receiving a region selecting instruction onto the posture image by a user (e.g., a radiographer). For example, the posture image is displayed on the display component, then the region selecting instruction is inputted onto the posture image by the radiographer (e.g., by performing a box selecting operation on the posture image using a mouse or other tools) to specify the detection field region of the dose estimation unit 23.

In some embodiments, the dose estimation unit 23 may be generally arranged on the detector 20 and its position is relatively fixed. Therefore, the detector 20 may also be identified from the posture image, and the detection field region of the dose estimation unit 23 may be determined based on the identified detector 20 in step 110.

In some embodiments, the processor 30 can obtain information about whether the dose estimation unit 23 is turned on or off; accordingly, in step 110, the acquisition of the detection field region of the dose estimation unit 23 may include determining which dose estimation units 23 are turned on first and then determining respective detection field region of the turned-on dose estimation units 23.

The body position of the object under examination presented in the posture image may refer to what kind of shooting body position of the object under examination in the posture image.

In some embodiments, in step 110, the object under examination may be identified from the posture image, and the body position of the object under examination presented in the posture image may be determined based on the identified object under examination. The identification of the object under examination from the posture image and the determination of the body position may be based on methods like machine learning.

In some embodiments, in step 110, after the object under examination is identified from the posture image, the detector 20 may then be identified and then the anatomical structure of the object under examination within the imaging plane region of the detector 20 may be identified, thereby determining the body position of the object under examination presented in the posture image.

The posture requirement(s) may refer to the posture of the to-be-examined position of the object under examination in relation to the object under examination.

Taking the to-be-examined position being a posterior anterior chest (PA chest) as an example, the posture requirement(s) of the body position may include the object under examination placing his/her hands on his/her hip, or embracing the imaging plane with bending both elbows forward as much as possible, turning both shoulders inward and laying them flat.

Taking the to-be-examined position being knee joint lateral position as an example, the posture requirement(s) of the body position may include the object under examination bending knees 120-130 degrees.

The current posture information about the object under examination associated with the posture requirement(s) may refer to the posture requirement(s) associated with the to-be-examined position, which requires which anatomical structures to have corresponding postures, and what postures these anatomical structures of the object under examination presented in the posture image.

Taking the to-be-examined position being a posterior anterior chest (PA chest) as an example, the posture requirement(s) of the body position may include the object under examination placing his/her hands on his/her hip, or embracing the imaging plane with bending both elbows forward as much as possible, turning both shoulders inward and laying them flat; accordingly, the current posture information about the object under examination associated with the posture requirement(s) may include: posture information about the position of hands and about the position of both shoulders of the object under examination in the posture image.

Taking the to-be-examined position being knee joint lateral position as an example, the posture requirement(s) of the body position may include the object under examination bending knees 120-130 degrees; accordingly, the current posture information about the object under examination associated with the posture requirement(s) may include: posture information about both knees of the object under examination in the posture image.

In some embodiments, in step 110, the posture requirement(s) associated with the to-be-examined position of the object under examination may be obtained, the anatomical structure associated with the to-be-examined position of the object under examination (or the anatomical structure associated with the posture requirement(s)) may be identified from the posture image, and the current posture information about the object under examination associated with the posture requirement(s) may be determined based on the posture requirement(s) and the identified anatomical structure.

The foreign object affecting imaging may refer to whether there is a foreign object on the object under examination or within the ROI in the posture image; and affecting imaging may refer to affecting the detector 20 to receive radiation.

For example, the object under examination may wear a necklace or other metal matters.

In some embodiments, in step 110, the posture image may be displayed, and the foreign object affecting imaging may be determined by receiving a foreign object selecting instruction onto the posture image by a user (e.g., a radiographer). For example, the posture image is displayed on the display component, then the region selecting instruction is inputted onto the posture image by the radiographer (e.g., by performing a click operation on the posture image using a mouse or other tools) to specify the foreign object on the posture image.

In some embodiments, in step 110, the foreign object affect imaging may be automatically identified from the posture image based on algorithms such as machine learning.

The above is some descriptions of the items concerning posture.

Step 120: performing posture quality control.

For example, in step 120, range information and/or position information about the ROI, the imaging plane region, and the radiation field region may be obtained based on the items concerning posture. The range information and/or the position information may be used for performing posture quality control.

The range information here may include the area of the region, and the location information here may include the location of the region, including the position of the center of the region and the position of four corners of the region (in the case of the region being a rectangle).

In some embodiments, performing posture quality control based on the range information and/or the position information in step 120 may include: calculating a position matching degree based on the range information and/or the position information; and performing posture quality control by displaying the position matching degree in step 120. The position matching degree may include a position matching degree between the ROI and the imaging plane region, and a position matching degree between the ROI and the radiation field region.

The position matching degree between the ROI and the imaging plane region may include: a position difference between the centers of the ROI and the imaging plane region; and/or, the degree of overlap between the ROI and the imaging plane region, such as a distance between their corresponding boundaries.

The position matching degree between the ROI and the radiation field region may include: a position difference between the centers of the ROI and the radiation field region; and/or, the degree of overlap between the ROI and the radiation field region, such as a distance between their corresponding boundaries.

In some embodiments, at least one of the items concerning posture and the position matching degree may be displayed in step 120. For example, at least one of the items concerning posture and the position matching degree may be displayed via the display component. In some embodiments, in step 120, posture quality control may be performed by displaying one or more of the items concerning posture.

For example, in step 120, one or more of the ROI, the imaging plane region, the radiation field region, the position matching degree, the body position of the object under examination presented in the posture image, the to-be-examined position of the object under examination, the detection field region, the posture requirement(s) associated with the to-be-examined position of the object under examination, the current posture information about the object under examination associated with the posture requirement(s), and the foreign object may be displayed via the display screen 50.

For example, in step 120, one or more of the ROI, the imaging plane region, the radiation field region, the position matching degree, the body position of the object under examination presented in the posture image, the to-be-examined position of the object under examination, the detection field region, the posture requirement(s) associated with the to-be-examined position of the object under examination, the current posture information about the object under examination associated with the posture requirement(s) and the foreign object may be displayed via the display of a computer.

In some embodiments, the ROI may be displayed by displaying a schematic graph (such as a region defined by lines). In some embodiments, the ROI may be displayed in a form of text and coordinate; for example, displaying the coordinates of the center of the ROI, or the coordinates of the four corners of the ROI (in the case where the ROI is a rectangle).

In some embodiments, the imaging plane region may be displayed by displaying a schematic graph (such as a region defined by lines). In some embodiments, the imaging plane region may be displayed in a form of text and coordinate; for example, displaying the coordinates of the center of the imaging plane region, or the coordinates of the four corners of the imaging plane region.

In some embodiments, the radiation field region may be displayed by displaying a schematic graph (such as a region defined by lines). In some embodiments, the radiation field region may be displayed in a form of text and coordinate; for example, displaying the coordinates of the center of the radiation field region, or the coordinates of the four corners of the radiation field region.

It shall be understood that when displaying such as the ROI, the imaging plane region, and the radiation field region using coordinates, the origins of their coordinate systems may be the same. For example, these regions may be displayed in the same image, and then a coordinate system may be established with the origin thereof being the center of the image, a point in the lower left corner of the image, or a point in the upper left corner of the image.

In some embodiments, the position matching degree may be displayed by labeling a deviation size on a region defined by lines; the deviation size may include one or more of a boundary deviation size, a corner deviation size and a center deviation size.

For example, in the case of displaying the ROI and the imaging plane region by a region defined by lines, the position matching degree between the ROI and the imaging plane region may be displayed by labeling the deviation size on a region defined by lines, wherein the deviation size may include one or more of: a deviation size between corresponding boundaries of the ROI and the imaging plane region, a deviation size between corresponding corners of the ROI and the imaging plane region, and a deviation size between centers of the ROI and the imaging plane region.

For another example, in the case of displaying the ROI and the radiation field region by a region defined by lines, the position matching degree between the ROI and the radiation field region may be displayed by labeling the deviation size on a region defined by lines, wherein the deviation size may include one or more of: a deviation size between corresponding boundaries of the ROI and the radiation field region, a deviation size between corresponding corners of the ROI and the radiation field region, and a deviation size between centers of the ROI and the radiation field region.

For yet another example, in the case of displaying the imaging plane region and the radiation field region by a region defined by lines, the position matching degree between the imaging plane region and the radiation field region may be displayed by labeling the deviation size on a region defined by lines, wherein the deviation size may include one or more of: a deviation size between corresponding boundaries of the imaging plane region and the radiation field region, a deviation size between corresponding corners of the imaging plane region and the radiation field region, and a deviation size between centers of the imaging plane region and the radiation field region.

In some embodiments, the position matching degree may be displayed in a form of text and coordinate. For example, with regard to the position matching degree between the ROI and the imaging plane region, coordinates of the centers of the two regions may be obtain, and a position difference between the centers of the two regions may be calculated to form a new coordinate. For example, the coordinate of the center of the ROI is (x1, y1), and the coordinate of the center of the imaging plane region is (x2, y2), then the position difference between the centers of the two regions is calculated to form a new coordinate (x1-x2, y1-y2). Alternatively, the difference between the corresponding angles of the ROI and the imaging plane region may be calculated to form a new coordinate to represent the position matching degree. So does the position matching degree between the ROI and the radiation field region, as well as the position matching degree between the imaging plane region and the radiation field region, which will not be repeated here.

In some embodiments, the body position of the object under examination presented in the posture image may be displayed in a form of text.

In some embodiments, the to-be-examined position of the object under examination may be displayed in a form of text.

In some embodiments, the detection field region may be displayed by displaying a schematic graph (such as a region defined by lines). In some embodiments, the detection field region may be displayed in a form of text and coordinate. For example, the coordinate of the center of the detection field region may be displayed, or the coordinates of the four corners of the detection field region may be displayed.

In some embodiments, the posture requirement(s) associated with the to-be-examined position of the object under examination may be displayed in a form of graphics and/or text.

In some embodiments, the current posture information about the object under examination associated with the posture requirement(s) may be displayed in a form of text.

In some embodiments, a foreign object affecting imaging may be displayed in a form of text or graphics. It shall be understood that the foreign object may be display only when it exists.

In some embodiments, a posture quality control image containing an auxiliary image may be generated and displayed in step 120. The auxiliary image may be the posture image or a schematic image obtained based on the posture image. The schematic image obtained based on the posture image may be the image that can be acquired by obtaining a contour of the object under examination and that of the detector based on the posture image, and then displaying an image containing the contour of the object under examination and that of the detector. In some embodiments, the posture quality control image may contain one or more of the items concerning posture. In some embodiments, the posture quality control image may contain the position matching degree. In some embodiments, the posture quality control image may contain the to-be-examined position of the object under examination.

For example, one or more of the ROI, the imaging plane region, the radiation field region and the detection field region may be displayed by superimposing a schematic graph on the auxiliary image. In some embodiments, the schematic graph may include a region defined by lines. Different regions (e.g., the ROI, the imaging plane region and the radiation field region) may be distinguished by using different types of lines and/or different colors of lines. The types of lines may refer to solid lines, dotted lines, and so on.

Further, the position matching degree may be displayed by labeling the deviation size on the posture quality control image by using a region defined by lines.

In some embodiments, in the case of there being the foreign object affecting imaging, the foreign object may be displayed by outlining or circling it on the auxiliary image that is included in the posture quality control image.

In some embodiments, at least one of the items concerning posture and the position matching degree may be displayed by projection in step 120. For example, the ROI may be displayed by projecting to the object under examination in step 120, wherein the position of the projected displayed ROI may be coincided with the position of the actual region of interest of the object under examination. For example, the imaging plane region may be displayed by projecting to the object under examination in step 120, wherein the position of the projected displayed imaging plane region may be coincided with the position of the actual imaging plane region of the detector. For example, the radiation field region may be displayed by projecting to the object under examination in step 120, wherein the position of the projected displayed radiation field region may be coincided with the position of the actual radiation field region of the radiation source. For example, the detection field region may be displayed by projecting to the object under examination in step 120, wherein the position of the projected displayed detection field region and the actual detection field region of the dose estimation unit. For example, the position matching degree may be displayed by projecting to the object under examination in step 120.

In an example of displaying some items concerning posture by projection, it shall be understood that it may include the processor 30 sending projection information to a projection device connected thereto, or the device itself including the projection device.

In some embodiments, performing posture quality control based on the range information and/or the position information in step 120 may include: obtaining QC result items including an imaging plane QC result item and a radiation field QC result item by performing quality control based on the range information and/or the position information of the ROI, the imaging plane region and the radiation field region, performing posture quality control by displaying the imaging plane QC result item and the radiation field QC result item in step 120.

In some embodiments, the QC result items may be obtained by performing quality control based on items concerning posture in step 120, the QC result items may further include one or more of: a detection field QC result item, a body position QC result item, a posture QC result item and a foreign object QC result item.

The following is a description of each of the QC result items.

The imaging plane QC result item may be a QC result indicating whether the ranges and/or positions of the ROI and the imaging plane region meet requirement. Whether the ranges of the ROI and the imaging plane region meet requirement may refer to the degree of overlap therebetween, such as a distance between corresponding boundaries of the two. Whether the positions of the ROI and the imaging plane region meet requirement may refer to a position difference between the centers of the two regions.

In some embodiments, the imaging plane QC result item may be used for indicating whether the centers of the ROI and the imaging plane region are within a preset deviation. In some embodiments, the imaging plane QC result item may be used for indicating whether the boundaries of the ROI and the imaging plane region are within a preset deviation.

For example, when the centers of the ROI and the imaging plane region are within a preset deviation, it may mean that the positions of the ROI and the imaging plane region meet requirement. For another example, when the boundaries of the ROI and the imaging plane region (which may refer to all corresponding boundaries) are within a preset deviation, it may mean that the ranges of the ROI and the imaging plane region meet requirement.

The radiation field QC result item may be a QC result indicating whether the ranges and/or positions of the ROI and the radiation field region meet requirement. Whether the ranges of the ROI and the radiation field region meet requirement may refer to the degree of overlap therebetween, such as a distance between corresponding boundaries of the two. Whether the positions of the ROI and the radiation field region meet requirement may refer to a position difference between the centers of the two regions.

In some embodiments, the radiation field QC result item may be used for indicating whether the centers of the ROI and the radiation field region are within a preset deviation. In some embodiments, the radiation field QC result item may be used for indicating whether the boundaries of the ROI and the radiation field region are within a preset deviation.

For example, when the centers of the ROI and the radiation field region are within a preset deviation, it may mean that the positions of the ROI and the radiation field region meet requirement. For another example, when the boundaries of the ROI and the radiation field region (which may refer to all corresponding boundaries) are within a preset deviation, it may mean that the ranges of the ROI and the radiation field region meet requirement.

The body position QC result item may be a QC result indicating whether the body position of the object under examination presented in the posture image meets requirement. In some embodiments, the body position QC result item may be used for indicating whether the body position of the object under examination presented in the posture image is the to-be-examined position of the object under examination.

For example, when the to-be-examined position of the object under examination is PA chest, and the body position of the object under examination presented in the posture image is also PA chest, it may mean that the body position of the object under examination presented in the posture image meets requirement and the quality control thereof is passed; otherwise, it may mean that it fails to meet requirement and the quality control fails.

The posture QC result item may be a QC result indicating whether the current posture information about the object under examination associated with the posture requirement (s) meets requirement. In some embodiments, the posture QC result item is used for indicating whether, in the current posture information about the object under examination associated with the posture requirement(s), posture information about the anatomical structure associated with (in relation to) a to-be-examined position of the object under examination may be conformed to a posture required by the posture requirement(s) associated with the to-be-examined position of the object under examination.

Taking the to-be-examined position being a posterior anterior chest (PA chest) as an example, the posture requirement(s) of the to-be-examined position may include the object under examination placing his/her hands on his/her hip, or embracing the imaging plane with bending both elbows forward as much as possible, turning both shoulders inward and laying them flat. Accordingly, the posture information about the anatomical structure associated with (in relation to) the posture requirement(s) associated with the to-be-examined position of the object under examination, such as posture information about both hands, elbows and shoulders, may be obtained to calculate a height difference between the shoulder peaks on both sides, and an open angle between the elbows to determined whether the posture information about the anatomical structure meets postures required by the posture requirement(s).

Taking the to-be-examined position being knee joint lateral position as an example, the posture requirement(s) thereof may include the object under examination bending knees 120-130 degrees; accordingly, the anatomical structure associated with the posture requirement(s) may be recognized, including recognition and calculation of the knee flexion angle to determine whether the posture information about the anatomical structure meets the posture required by the posture requirement(s).

The detection field QC result item may be a QC result indicating whether the detection field region is within the ROI and/or whether the detection field region is a detection field region that should be selected to be opened.

The foreign object QC result item may be a QC result indicating whether there is a foreign object and/or whether there is a foreign object in the ROI.

In some embodiments, the posture quality control image containing the auxiliary image may be generated and display in step 120. The auxiliary image may be the posture image or the schematic image obtained based on the posture image. The schematic image obtained based on the posture image may be the image that can be acquired by obtaining a contour of the object under examination and that of the detector based on the posture image, and then displaying an image containing the contour of the object under examination and that of the detector. In some embodiments, the posture quality control image may contain one or more of the QC result items.

In some embodiments, the to-be-examined position of the object under examination may be selected on the human-computer interaction interface by radiographers. Referring to FIG. 11, the radiographic imaging method in some embodiments may further include the following steps:

step 180: displaying the detectable body part of the object under examination on the human-computer interaction interface; and step 190: in response to a selection instruction on the detectable body part, the to-be-examined position of the object under examination may be determined from the detectable body part.

Figures 12, 13:
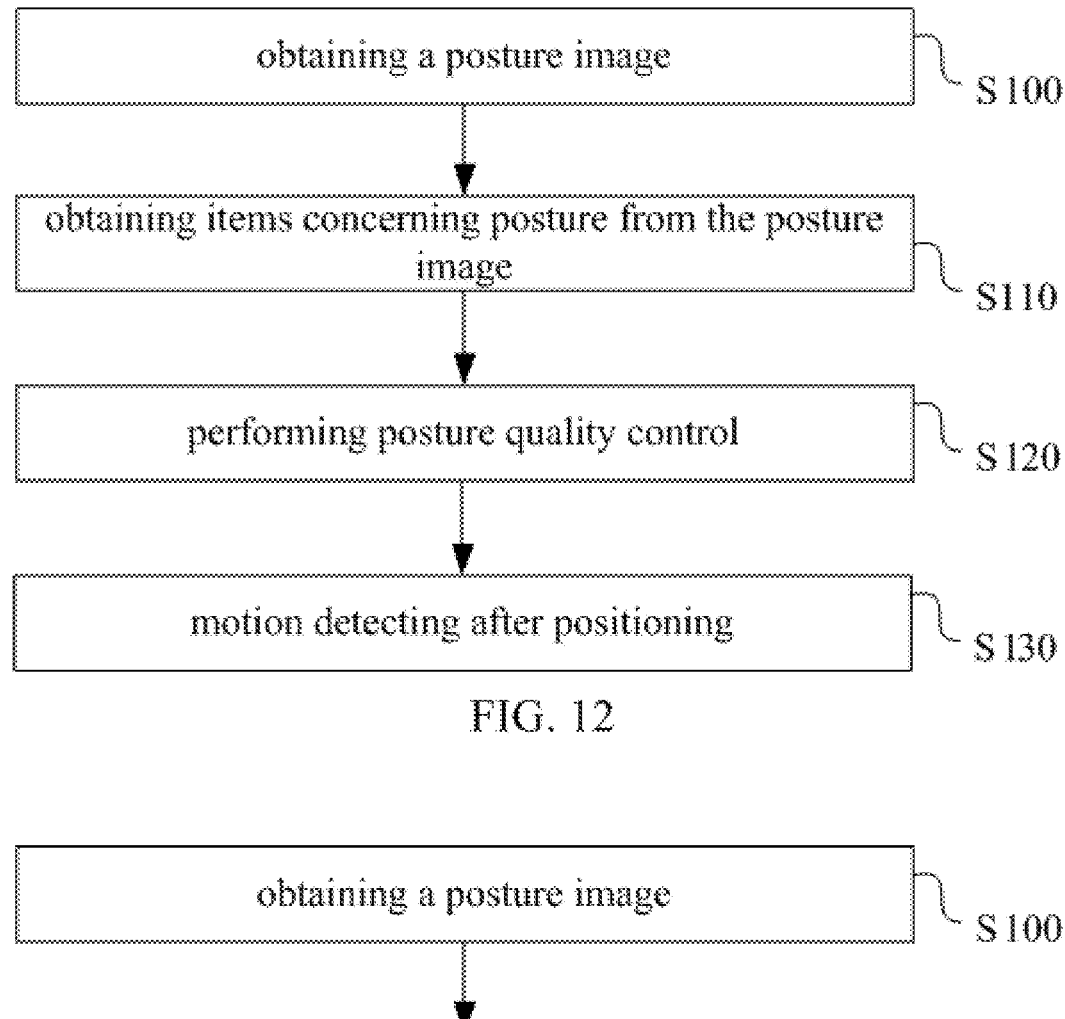
FIG. 12 is a schematic flowchart of a radiographic imaging method in some embodiments.
FIG. 13 is a schematic flowchart of a radiographic imaging method in some embodiments.

Referring to FIG. 12, the radiographic imaging method in some embodiments may further include step 140: motion detection after positioning. In step 130, the posture image after positioning may be obtained, the movement of the object under examination may be determined based on the posture image after positioning and the subsequent obtained posture image, and when determining that the object is moving, prompt information for indicating a motion state may be generated.

For example, in step 130, based on the posture images of different frames, the positions of features in the images (e.g., contours and keypoints) may be recognized, and their position changes among the posture images of different frames may be compared, thereby obtaining a moving distance and a moving velocity to form a moving trajectory. Alternatively, differences of corresponding pixels in a certain region of the images over a period of time may be determined so as to obtain the moving distance and velocity.

Referring to FIG. 13, in some embodiments, the radiographic imaging method may further include step 140: obtaining and outputting a prompt item. For example, in step 140, the prompt item may be obtained based on the QC result items, and then outputted, wherein the prompt item may be used for indicating a result caused due to the control result items failing to meet requirements. The prompt item may be outputted by display and/or voice playback.

The prompt item may be generated and outputted when the QC result items fail to meet requirements to indicate the result caused due to the QC result items failing to meet requirements, which helps radiographers with less experience to better perform subsequent positioning operations. For example, when the imaging plane QC result item fails to meet requirement, the prompt item may include radiographic image center offset and anatomical truncation; when the radiation field QC result item fails to meet requirement, the prompt item may include radiographic image center offset, anatomical truncation, and excessive irradiation (radiation) area; when the detection field QC result item fails to meet requirement, the prompt item may include insufficient dose for images; when the foreign object QC result item fails to meet requirement, that is there is a foreign object and/or there is a foreign object in the ROI, the prompt item may include possible obstruction of the diagnostic region; when the body position QC result item fails to meet requirement, the prompt item may include error radiograph for positioning; and when the posture QC result item fails to meet requirement, the prompt item may include non-standard posture.

Figure 14:
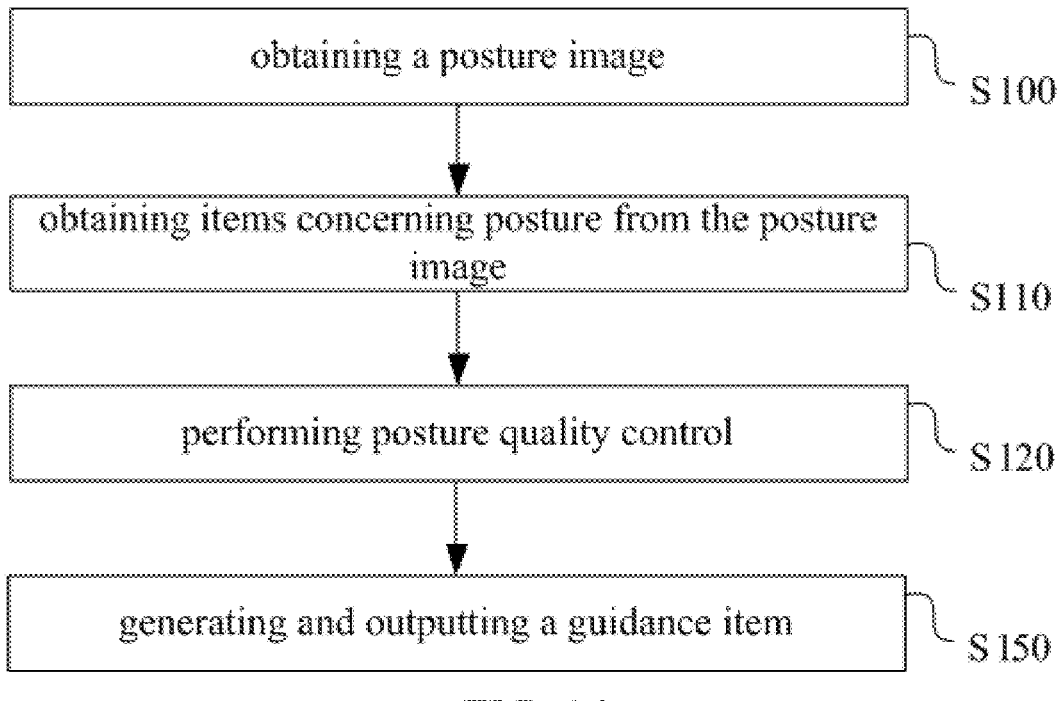
FIG. 14 is a schematic flowchart of a radiographic imaging method in some embodiments.

Referring to FIG. 14, in some embodiments, the radiographic imaging method may also include step 150: generating and outputting a guidance item, and/or controlling an execution action of a device based on the guidance item. For example, in step 150, the guidance item used for indicating an execution action to be guided due to the QC result items failing to meet requirements may be obtained based on the QC result items.

In some embodiments, the guidance item may at least include at least one of: a guidance prompt for a position and/or an angle of the detector; a guidance prompt for a position and/or an angle of the radiation source; a guidance prompt for the size of the radiation field region; a guidance prompt for selecting the detection field region; a prompt for guiding movement of the object under examination so that the imaging plane QC result item and/or the radiation field QC result item meet requirements; and a prompt for guiding the posture of the object under examination so that the body position QC result item and the posture QC result item meet requirements.

The guidance item may be outputted by display and/or voice playback.

In some embodiments, the guidance item may include two types of guidance items, such as a first type of guidance item used for being outputted (e.g. being outputted by display and/or voice playback) to guide the object under examination or radiographers and a second type of guidance item which may be obtained by the processor 30 to control corresponding components of the apparatus to execute corresponding actions so that the QC result items meet requirements.

In the case of non-standard posture by the radiographer, the processor 30 may guide the position and angle of the detector 20, the position and range of the radiation field region of the radiation source 10, the position and angle of the radiation source 10, and the selection (on/off) of the dose estimation unit 23.

The radiographer may manually modify based on the guidance item.

In some embodiments, the posture image may be an image acquired in real time, and when the posture image changes, the items concerning posture may be updated in real time. In some embodiments, the position matching degree may also be updated in real time.

In some embodiments, the posture image may be an image acquired in real time, and when the posture image changes, the QC result items may be updated in real time. In some embodiments, the prompt item and/or the guidance item may also be updated in real time.

Here are some examples.

Figure 15A:
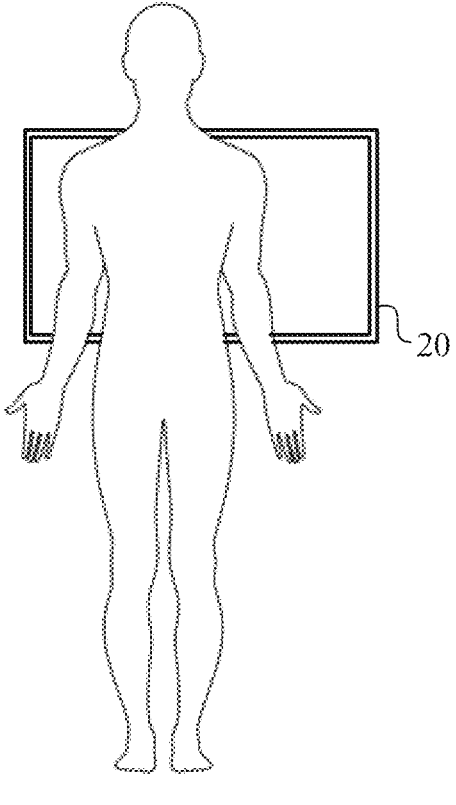
FIG. 15(a) is an example diagram of a posture image in some embodiment.

Referring to FIG. 15(a) schematically showing the posture image, the chest of the object under examination is closely attached to the detector 20, located at the shooting position between the detector 20 and the radiation source 10 (not shown in the figure).

FIG. 15(b) shows an example of the posture quality control image 100. The posture quality control image 100 contains an auxiliary image which is the posture image or a schematic diagram thereof. The ROI, the imaging plane region, the radiation field region and the detection field region may be displayed by being superimposed on the auxiliary image. In the figure, the ROI may be represented by a region 01 defined by a solid box, the imaging plane region of the detector 20 may be represented by a region 02 defined by a dotted box, the radiation field region of the radiation source 10 may be represented by a region 03 defined by a dashed box, the detection field region of the dose estimation unit 23 may be represented by a region 04 defined by a gray filled rectangle. There are three detection field regions of the dose estimation unit 23 in the figure. The body position of the object under examination presented in the posture image, the to-be-examined position of the object under examination, the position matching degree, the posture requirement(s) and the current posture information about the object under examination associated with the posture requirement(s) may also be displayed in the posture quality control image 100. In the figure, the "body position in image" may represent the body position of the object under examination presented in the posture image; and the "to-be-examined position" may refer to the body position of the object under examination actually required to be examined, for example the to-be-examined position selected from the object under examination via the human-computer interaction interface by the radiographer. In the posture quality control image 100, the "center difference (120,30)" between the ROI and the imaging plane region may refer to the distance in coordinates of the centers of the ROI and the imaging plane region, with the difference in the X axis coordinate being 120 and the difference in the Y axis coordinate being 30, both in millimeters; the "edge difference (54, 60, 184, 20)" of the ROI and the imaging plane region may refer to the distance between the boundaries of the ROI and the imaging plane region (since these two regions are rectangular in the image, the corresponding boundaries are: top, bottom, left and right), with the edge/boundary difference being 54, 60, 184, 20, respectively, all in millimeters. Similarly, in the posture quality control image 100, the "center difference (120,30)" between the ROI and the radiation field region may refer to the distance in coordinates of the centers of the ROI and the radiation field region, with the difference in the X axis coordinate being 120 and the difference in the Y axis coordinate being 30, both in millimeters; the "edge difference (54, 60, 184, 10)" of the ROI and the radiation field region may refer to the distance between the boundaries of the ROI and the radiation field region (since these two regions are rectangular in the image, the corresponding boundaries are: top, bottom, left and right), with the edge/boundary difference being 54, 60, 184, 10, respectively, all in millimeters. It should be noted that these values in the figure are only used for illustrative examples. In the posture quality control image 100, the "current posture" may refer to the current posture information about the object under examination associated with the posture requirement(s).

Figure 15C:
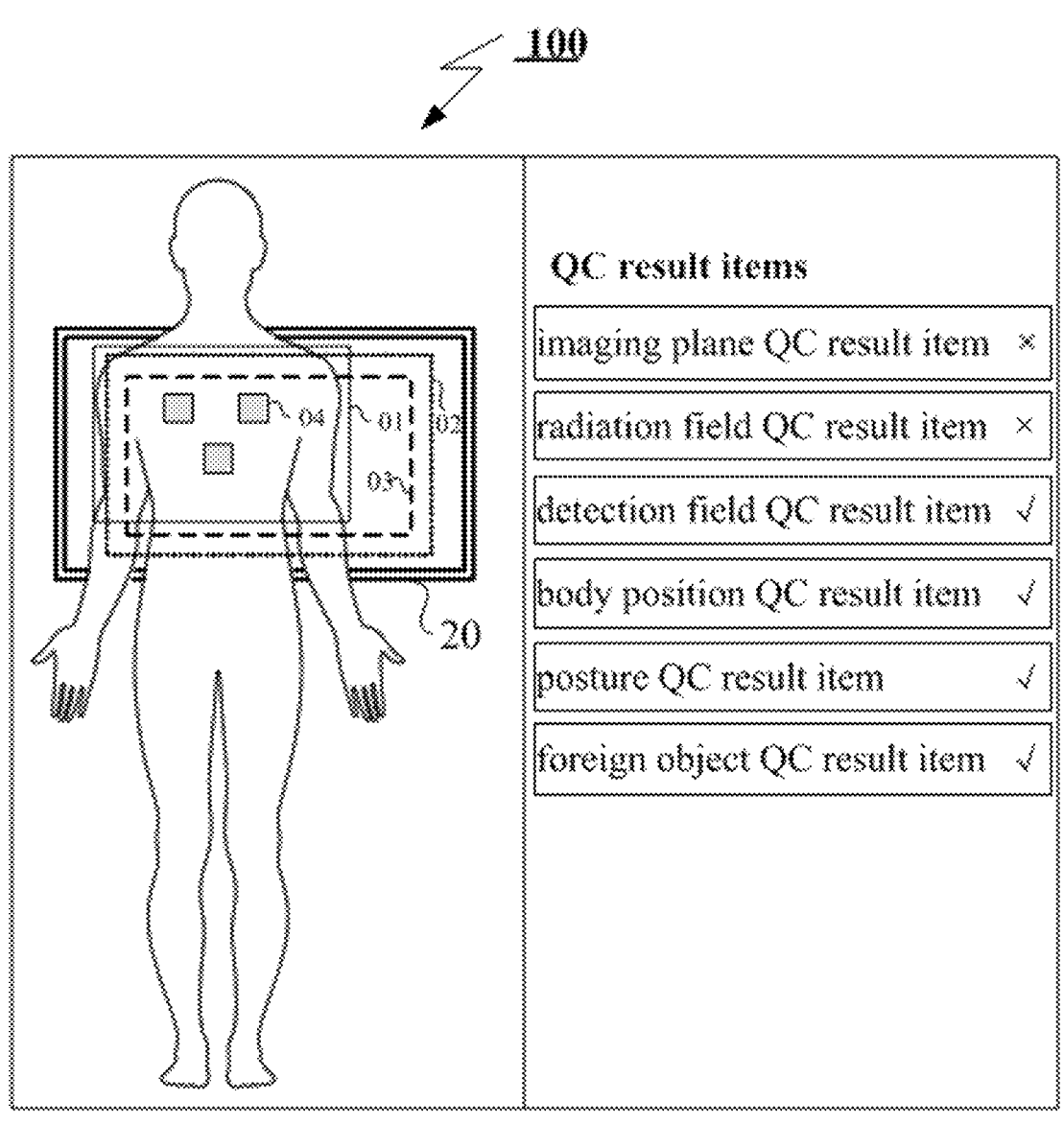
FIG. 15(c) is an example diagram of a posture quality control image in some embodiment.
Figure 15D:
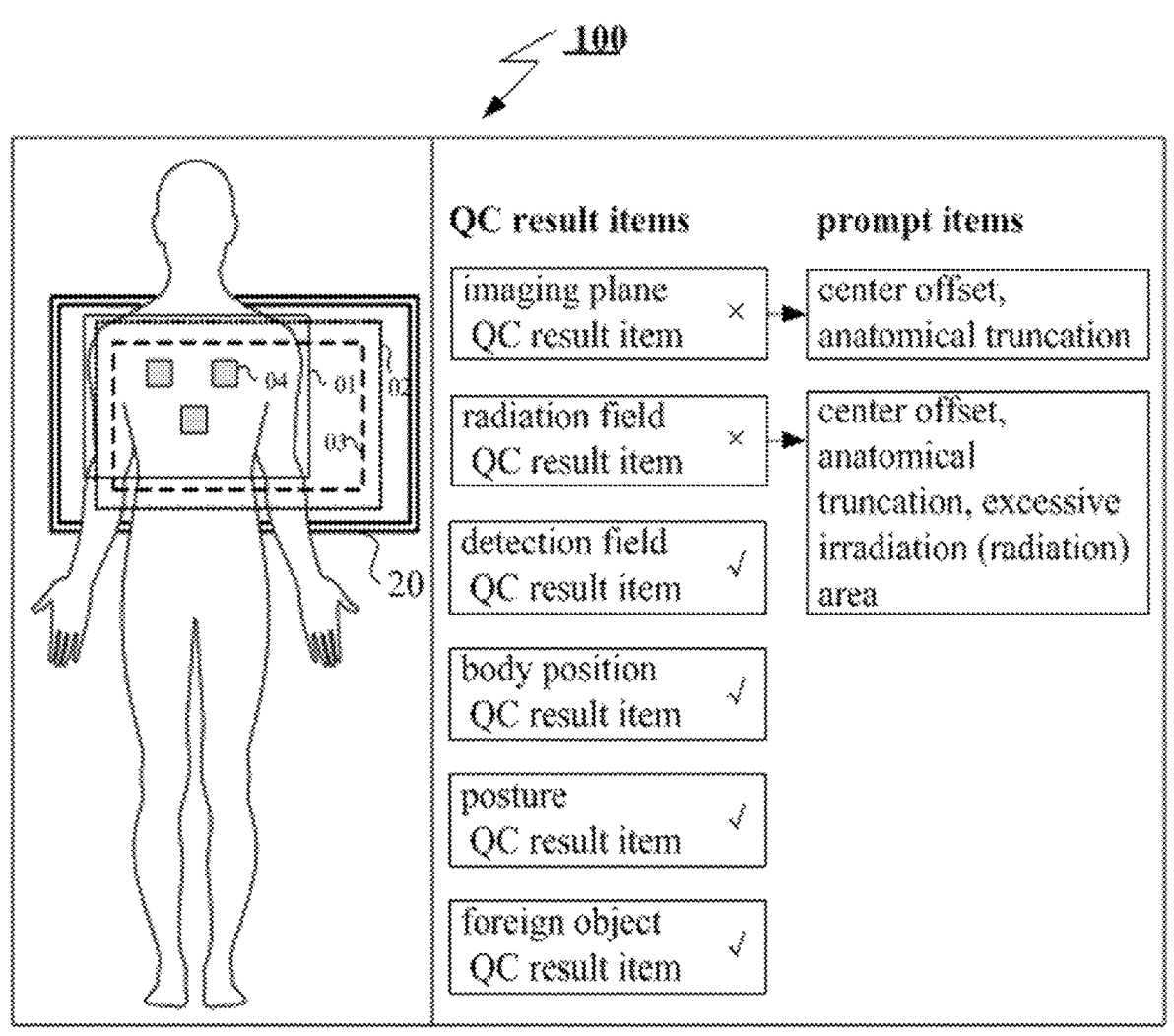
FIG. 15(d) is an example diagram of a posture quality control image in some embodiment.

FIG. 15(*c*) shows an example of the posture quality control image 100. The posture quality control image 100 contains an auxiliary image which is the posture image or a schematic diagram thereof. The QC result items displayed in the posture quality control image 100 with a tick behind may indicate that the corresponding QC result items meet requirements, and the QC result items with a cross behind may indicate that the corresponding QC result items fail to meet requirements. In addition, the ROI, the imaging plane region, the radiation field region and the detection field region may be displayed by being superimposed on the auxiliary image. In the figure, the ROI may be represented by a region 01 defined by a solid box, the imaging plane region of the detector 20 may be represented by a region 02 defined by a dotted box, the radiation field region of the radiation source 10 may be represented by a region 03 defined by a dashed box, the detection field region of the dose estimation unit 23 may be represented by a region 04 defined by a gray filled rectangle. There are three detection field regions of the dose estimation unit 23 in the figure.

FIG. 15(*d*) shows an example of a posture quality control image 100, with prompt items also displayed on the posture quality control image 100. Since the imaging plane QC result item and the radiation field QC result item fail to meet requirements, both corresponding prompt items are displayed in the figure.

FIG. 15(*e*) shows an example of a posture quality control image 100, with multiple items concerning posture displayed on the posture quality control image 100. The "body position in image" may represent the body position of the object under examination presented in the posture image; and the "to-be-examined position" may refer to the body position of the object under examination actually required to be examined, for example the to-be-examined position selected from the object under examination via the human-computer interaction interface by the radiographer.

FIG. 16 shows another example of a posture quality control image 100. The ROI, the imaging plane region and the radiation field region may be displayed by a region defined by lines on the posture image that is included in the posture quality control image 100, and the position matching degree may be displayed by labeling the deviation size via a region defined by lines. As can be seen in the figure, the object under examination is standing directly in front of the detector 20, with a small-dashed box representing the radiation field region, a large-dashed box representing the imaging plane region, and a solid box representing the ROI. In the figure, it can be seen that the centers of the radiation field region and the imaging plane region are coincident, while the center of the ROI is 120 mm away from the centers of the two regions, the left boundary of the ROI is 54 mm away from the left boundary of the imaging plane region, and the left boundary of the ROI is 104 mm away from the left boundary of the radiation field region.

FIG. 17 shows an example of posture requirement(s) s, which may be explained by displaying a standard posture image with text descriptions.

FIG. 18 is an example of displaying items concerning posture by projection. In the figure, the ROI is directly projected onto the object under examination, with the position of the projected displayed ROI being coincided with the position of the actual region of interest of the object under examination.

FIG. 19(*a*) is an example of a posture quality control image 100. In the figure, the "QC items" may represent the QC result items, the "center and range of imaging plane" may represent the imaging plane QC result item, the "center and range of radiation field" may represent the radiation field QC result item, the "selection of ionization chamber" may represent the detection field QC result item, the "no non-medical foreign object" may represent the foreign object QC result item, the "current position in accord with selected position" may represent the body position QC result item, and the "correct posture requirement(s) for specific position" may represent the posture QC result item. The items may be marked with different background colors to indicate whether corresponding QC result items meet requirements or not; for example, the QC result item with a red background may indicate that it fails to meet requirement, and it may meet the requirement with a green background. FIG. 19(*b*) is an example of a posture quality control image 100, in which the QC result items with a tick behind may indicate that the corresponding QC result items meet requirements, and the QC result items with a cross behind may indicate that the corresponding QC result items fail to meet requirements.

Figure 20B:
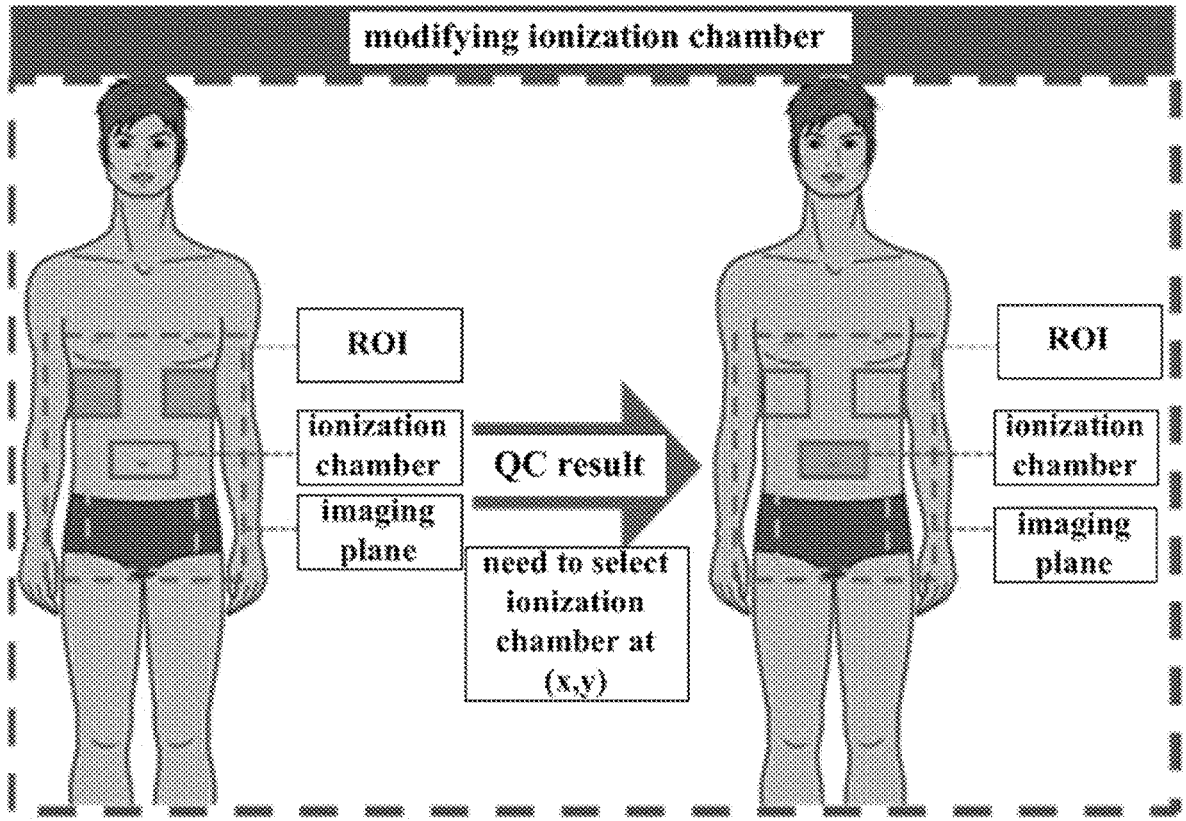
FIG. 20(b) is an example diagram of displaying a guidance item in some other embodiment.

FIG. 20(*a*) shows an example of guidance items, which is used to illustrate the guidance item corresponding to the imaging plane QC result item, and the guidance item corresponding to the radiation field QC result item. In FIG. 20(*a*), the left area displays a schematic diagram of a object under examination in a manner associated with his/her to-be-examined position; and since it is the chest of the object under examination that needs to be radiographed in the figure, three items concerning posture are displayed in the schematic diagram of the object under examination, as shown by the three dashed boxes outlined around the object under examination. These three dashed boxes are from top to bottom, representing the ROI, the imaging plane region and the radiation field region. It can be seen that the center of the ROI is relatively far from the centers of the other two regions in the figure, which may be detected with quality control by the imaging plane QC result item and the radiation field QC result item, then corresponding guidance items may be generated to prompt that the detector 20 (e.g. a flat panel detector) need to be moved upward n centimeters, as well as the radiation source 10 needed to be moved so that its radiation field region moved upward n centimeters. The new positions of predicted ROI, imaging plane region and radiation field region acquired after movement are displayed on the right side of the figure. The detector 20 and/or the radiation source 10 may be controlled to move manually by a radiographer or automatically by the apparatus based on the guidance items. FIG. 20(b) shows an example of a guidance item, which is used to illustrate the guidance item corresponding to the detection field QC result item. In FIG. 20(b), the left area displays a schematic diagram of an object under examination, with a ROI and an imaging plane region shown on the body of the object under examination and the imaging plane QC result item being met requirement. There are also three estimated detection field regions shown on the body of the object, which are illustrated by using the ionization chamber as an example as shown in figure. Assuming that in the three estimated detection field regions, the one thereof colored gray may indicate a turned-on detection field region and the one thereof not colored gray may indicate a turned-off detection field region; accordingly, the top two detection field regions are turned on and the lower detection field region is turned off on the body of the left object under examination. As the current to-be-examined position of the object under examination is required that the lower detection field region thereof is turned on and located within the ROI, the detection field QC result item may indicate that it fails to meet the requirement, generating a guidance item and prompting in the image to select the lower detection field region to turn on. This may be controlled manually by the radiographer to turn on and off the estimated detection field region, or automatically controlled by the apparatus based on the guidance item to turn on and off the estimated detection field region. The right side of the figure shows a corrected schematic diagram on the object under examination based on the guidance item.

FIGS. 21(a) and 21(b) show two examples of motion detection after positioning in step 130. In FIG. 21(a), an image of a correctly positioned posture is acquired and displayed, followed by the display of a real-time posture image, either separately or simultaneously, and motion detection is performed. The corresponding motion information, including displacement and/or velocity, is displayed next to the real-time posture image, such as the horizontal and vertical displacement (in millimeters) of the object under examination, as well as the motion velocity (e.g., the horizontal and vertical velocities) of the object under examination. FIG. 21(b) is similar to FIG. 21(a), except that besides the motion information such as displacement and velocity of the object under examination can be displayed next to the real-time posture image, such motion information can also displayed on the body of the object under examination, such as indicating the direction of displacement and velocity on the body of the object under examination through arrows, and labeling the corresponding velocity and displacement information.

The present disclosure has been illustrated by reference to various exemplary embodiments. However, those skilled in the art will recognize that the exemplary embodiments can be changed and modified without departing from the scope of the present disclosure. For example, the various operational steps and the components used to perform the operational steps can be implemented in different ways depending on a particular application or taking into account any number of cost functions associated with the operation of the system (for example, one or more steps can be deleted, modified or combined into other steps).

In the embodiments above, this may be accomplished, in whole or in part, by software, hardware, firmware, or any combination thereof. Furthermore, as will be understood by those skilled in the art, the principles of the present disclosure may be embodied in computer program products on computer readable storage media that are preloaded with computer readable program code. Any tangible, non-transitory computer readable storage media may be used, including magnetic storage devices (hard disks, floppy disks, etc.), optical storage devices (CD to ROM, DVD, Blu Ray disks, etc.), flash memory and/or the like. These computer program instructions may be loaded onto a general-purpose computer, a special purpose computer, or other programmable data processing device to form a machine so that the instructions executed on the computer or other programmable data processing device generate a device for achieving a specified function. These computer program instructions may also be stored in computer readable memory that may instruct the computer or other programmable data processing device to operate in a particular manner so that the instructions stored in the computer readable memory form a manufactured article including an implementing device for achieving a specified function." A computer program instruction may also be loaded into a computer or other programmable data processing device so as to cause a series of operation steps to be executed on the computer or other programmable device to produce a computer-implemented process, so that the instructions executed on the computer or other programmable device provide the steps for implementing a specified function.

Although the principles of the present disclosure have been shown in various embodiments, many modifications of the structure, arrangement, proportions, elements, materials and parts particularly suited to particular environmental and operational requirements may be used without departing from the principles and scope of this disclosure. The above modifications and other changes or modifications will be included within the scope of this disclosure.

The foregoing specific descriptions have been described with reference to various embodiments. However, those skilled in the art will recognize that various modifications and changes can be made without departing from the scope of this disclosure. Therefore, the consideration of this disclosure will be in an illustrative rather than a restrictive sense and all such modifications will be included within its scope. Also, the advantages, other advantages and solutions to problems with respect to various embodiments have been described above. However, neither the benefits, advantages, solutions to problems nor any elements that generate them or make them more explicit should be construed as critical, necessary or required. The term "include" as used herein, and any other variation thereof, is used non-exclusively so that a process, method, article or device including a list of elements includes not only those elements but also other elements that are not expressly listed or not incorporated into the process, method, system, article or device. Further, the term "couple" as used herein, and any other variation thereof, refers to physical connection, electrical connection, magnetic connection, optical connection, communication connection, functional connection and/or any other connection.

Those skilled in the art will realize that many changes in the details of the above embodiments can be made without departing from the basic principles of the present disclosure. Therefore, the scope of the present disclosure should be determined only by the claims.

The invention claimed is:

1. A radiographic imaging method, comprising:

obtaining a posture image of an object under examination located at a shooting position between a radiation source and a detector;

obtaining items concerning posture based on the posture image, the items concerning posture including a region of interest of the object under examination, an imaging plane region of the detector and a radiation field region of the radiation source on the object under examination;

obtaining range information and/or position information about the region of interest, the imaging plane region and the radiation field region based on the items concerning posture;

performing posture quality control using the range information and/or the position information, wherein the performing posture quality control using the range information and/or the position information comprises:

performing quality control based on the range information and/or the position information to obtain quality control result items including an imaging plane quality control result item and a radiation field quality control result item, the imaging plane quality control result item being a quality control result indicating whether a range and/or a position of the region of interest and that of the imaging plane region meet requirements, and the radiation field quality control result item being a quality control result indicating whether the range and/or the position of the region of interest and that of the radiation field region meet requirements; and performing posture quality control by displaying the imaging plane quality control result item and the radiation field quality control result item;

obtaining a guidance item based on the quality control result items, the guidance item being used for indicating an execution action to be guided due to the quality control result items failing to meet requirements; and outputting the guidance item, and/or controlling a device to carry out the execution action based on the guidance item.

2. The method according to claim 1, wherein the performing posture quality control using the range information and/or the position information further comprises:

calculating a position matching degree based on the range information and/or the position information, the position matching degree including: a position matching degree between the region of interest and the imaging plane region, and a position matching degree between the region of interest and the radiation field region; and performing posture quality control by displaying the position matching degree.

3. The method according to claim 1, wherein the items concerning posture further include one or more of:

a detection field region of a dose estimation unit, a body position of the object under examination presented in the posture image, posture requirement, current posture information about the object under examination associated with the posture requirement, and a foreign object affecting imaging.

4. The method according to claim 3, wherein the obtaining items concerning posture based on the posture image comprises:

displaying the posture image, receiving a region selecting instruction from a user on the posture image to determine the region of interest; or identifying an anatomical structure associated with a to-be-examined position of the object under examination from the posture image, and generating the region of interest based on the anatomical structure.

5. The method according to claim 3, wherein the obtaining items concerning posture based on the posture image comprises:

obtaining posture requirement associated with a to-be-examined position of the object under examination;

identifying an anatomical structure associated with the to-be-examined position of the object under examination from the posture image; and determining the current posture information about the object under examination associated with the posture requirement based on the posture requirement and the identified anatomical structure.

6. The method according to claim 3, further comprising:

obtaining quality control result items based on the items concerning posture, the quality control result items further comprising one or more of: a detection field quality control result item, a body position quality control result item, a posture quality control result item and a foreign object quality control result item;

the body position quality control result item being a quality control result indicating whether the body position of the object under examination presented in the posture image meets requirements, the posture quality control result item being a quality control result indicating whether the current posture information about the object under examination associated with the posture requirement meets requirements, the detection field quality control result item being a quality control result indicating whether the detection field region is within the region of interest and/or whether the detection field region is to be selected to be opened, and the foreign object quality control result item being a quality control result indicating whether there is a foreign object and/or whether there is a foreign object in the region of interest; and displaying one or more of the detection field quality control result item, the body position quality control result item, the posture quality control result item and the foreign object quality control result item.

7. The method according to claim 1, further comprising:
performing posture quality control by displaying one or more of the items concerning posture.

8. The method according to claim 7, wherein the displaying one or more of the items concerning posture comprises:
generating and displaying a posture quality control image comprising an auxiliary image, the posture quality control image further comprising one or more of the items concerning posture, and the auxiliary image being the posture image or a schematic image obtained based on the posture image.

9. The method according to claim 8, wherein
the region of interest, the imaging plane region and the radiation field region are displayed by superimposing a schematic graph onto the auxiliary image that is included in the posture quality control image, the schematic graph including a region defined by lines; and/or the region of interest, the imaging plane region, and the radiation field region are displayed in a form of text and coordinate on the posture quality control image; and/or a position matching degree is displayed in a form of text and coordinate on the posture quality control image.

10. The method according to claim 9, wherein the position matching degree is displayed by labeling a deviation size on a region defined by lines on the posture quality control image, the deviation size including one or more of: a boundary deviation size, a corner deviation size and a center deviation size.

11. The method according to claim 7, wherein the displaying one or more of the items concerning posture comprises: displaying by projection, wherein:

the region of interest is displayed by projecting it onto the object under examination, a position of the projected and displayed region of interest being coincided with a position of an actual region of interest of the object under examination; and/or the imaging plane region is displayed by projecting it onto the object under examination, a position of the projected and displayed imaging plane region being coincided with a position of an actual imaging plane region of the detector; and/or the radiation field region is displayed by projecting it onto the object under examination, a position of the projected and displayed radiation field region being coincided with a position of an actual radiation field of the radiation source; and/or a detection field region is displayed by projecting it onto the object under examination, a position of the projected and displayed detection field region being coincided with a position of an actual detection field region of a dose estimation unit; and/or a position matching degree is displayed by projecting it onto the object under examination.

12. The method according to claim 1, further comprising:

obtaining the posture image after positioning the object under examination at the shooting position between the radiation source and the detector at a first time, determining whether the object under examination is moving based on the posture image obtained after positioning and a second posture image obtained at a second time having an interval after the first time, and, when determining that the object under examination is moving, generating prompt information for indicating a motion state.

13. The method according to claim 1, wherein the posture image is acquired in real time, and when the posture image changes, the items concerning posture are updated in real time.

14. The method according to claim 1, wherein:

the imaging plane quality control result item is used for indicating: whether respective centers of the region of interest and the imaging plane region are within a preset deviation, and/or whether respective boundaries of the region of interest and the imaging plane region are within a preset deviation; and/or the radiation field quality control result item is used for indicating: whether respective centers of the region of interest and the radiation field region are within a preset deviation, and/or whether respective boundaries of the region of interest and the radiation field region are within a preset deviation; and/or a body position quality control result item is used for indicating whether a body position of the object under examination presented in the posture image is a to-be-examined position of the object under examination; and/or a posture quality control result item is used for indicating whether, in current posture information about the object under examination associated with posture requirement, posture information about an anatomical structure associated with a to-be-examined position of the object under examination is conformed to a posture required by the posture requirement associated with the to-be-examined position of the object under examination.

15. The method according to claim 1, further comprising:

obtaining a prompt item based on the quality control result items, the prompt item being used for indicating a result caused due to the quality control result items failing to meet the requirements; and outputting the prompt item.

16. The method according to claim 1, wherein the guidance item comprises at least one of:

a guidance prompt for a position and/or an angle of the detector;

a guidance prompt for a position and/or an angle of the radiation source;

a guidance prompt for a size of the radiation field region;

a guidance prompt for selecting a detection field region;

a prompt for guiding movement of the object under examination so that the imaging plane quality control result item and/or the radiation field quality control result item meet requirements; and a prompt for guiding a posture of the object under examination so that a body position quality control result item and/or a posture quality control result item meet requirements.

17. The method according to claim 1, further comprising:

displaying a detectable body part of the object under examination on a human-computer interaction interface; and in response to a selection instruction on the detectable body part, determining a to-be-examined position of the object under examination from the detectable body part.

18. A radiographic imaging apparatus, comprising:

a radiation source configured to emit radioactive rays to an object under examination;

a detector configured to receive the radioactive rays penetrating the object under examination; and a processor configured to:

obtain a posture image of the object under examination located at a shooting position between the radiation source and the detector;

obtain items concerning posture based on the posture image, the items concerning posture including a region of interest of the object under examination, an imaging plane region of the detector and a radiation field region of the radiation source on the object under examination;

obtain range information and/or position information about the region of interest, the imaging plane region and the radiation field region based on the items concerning posture;

perform posture quality control using the range information and/or the position information, wherein when performing the posture quality control using the range information and/or the position information, the processor is further configured to:

perform quality control based on the range information and/or the position information to obtain quality control result items including an imaging plane quality control result item and a radiation field quality control result item, the imaging plane quality control result item being a quality control result indicating whether a range and/or a position of the region of interest and that of the imaging plane region meet requirements, and the radiation field quality control result item being a quality control result indicating whether the range and/or the position of the region of interest and that of the radiation field region meet requirements; and perform posture quality control by displaying the imaging plane quality control result item and the radiation field quality control result item;

obtain a guidance item based on the quality control result items, the guidance item being used for indicating an execution action to be guided due to the quality control result items failing to meet requirements; and output the guidance item, and/or control a device to carry out the execution action based on the guidance item.

* * * * *